(12) United States Patent
Erkamp et al.

(10) Patent No.: US 11,660,064 B2
(45) Date of Patent: May 30, 2023

(54) INTRAVASCULAR ULTRASOUND POSITION IDENTIFICATION

(71) Applicant: KONINKLIJKE PHILIPS N.V., Eindhoven (NL)

(72) Inventors: Ramon Quido Erkamp, Swampscott, MA (US); Francois Guy Gerard Marie Vignon, Andover, MA (US); Shyam Bharat, Arlington, MA (US); Kunal Vaidya, Boston, MA (US); Ameet Kumar Jain, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/059,530

(22) PCT Filed: Jun. 17, 2019

(86) PCT No.: PCT/EP2019/065794
§ 371 (c)(1),
(2) Date: Nov. 30, 2020

(87) PCT Pub. No.: WO2019/243211
PCT Pub. Date: Dec. 26, 2019

(65) Prior Publication Data
US 2021/0298716 A1    Sep. 30, 2021

Related U.S. Application Data

(60) Provisional application No. 62/688,431, filed on Jun. 22, 2018.

(51) Int. Cl.
*A61B 8/00* (2006.01)
*A61B 8/08* (2006.01)
*A61B 8/12* (2006.01)

(52) U.S. Cl.
CPC ........... *A61B 8/0841* (2013.01); *A61B 8/12* (2013.01); *A61B 8/463* (2013.01)

(58) Field of Classification Search
CPC ......... A61B 8/0841; A61B 8/12; A61B 8/463; A61B 8/483
See application file for complete search history.

(56) References Cited

U.S. PATENT DOCUMENTS 5,546,949 A    8/1996   Frazin et al.
6,120,453 A    9/2000   Sharp
(Continued)

OTHER PUBLICATIONS

PCT/EP2019/065794 ISR & WO, Sep. 26, 2019, 13 Page Document.

*Primary Examiner* — Serkan Akar
*Assistant Examiner* — Amal Aly Farag

(57) ABSTRACT

A controller (310) for identifying positioning of an intravascular ultrasound probe (952) includes a memory (362) that stores instructions (884) and a processor (361) that executes the instructions (884). When executed by the processor (361), the instructions (884) cause the controller (310) to execute a process that includes receiving first signals from at least one element of the intravascular ultrasound probe (952). The process also includes receiving second signals from an external ultrasound probe. Based on the first signals and the second signals, the controller (310) determines a position of the intravascular ultrasound probe (952) in a tracking space that includes the intravascular ultrasound probe (952) and the external ultrasound probe.

17 Claims, 18 Drawing Sheets

(56) References Cited

U.S. PATENT DOCUMENTS

| | | | |
|---|---|---|---|
| 2002/0173720 A1 | 11/2002 | Seo et al. | |
| 2006/0270934 A1* | 11/2006 | Savord | G01S 15/8993 600/437 |
| 2007/0049827 A1* | 3/2007 | Donaldson | A61B 8/483 600/443 |
| 2014/0094695 A1* | 4/2014 | Jain | A61B 8/481 600/424 |
| 2014/0276684 A1* | 9/2014 | Huennekens | A61B 17/320758 606/7 |
| 2015/0173629 A1* | 6/2015 | Corl | A61B 5/02158 600/486 |
| 2019/0046156 A1* | 2/2019 | De Cicco | A61B 6/032 |

* cited by examiner

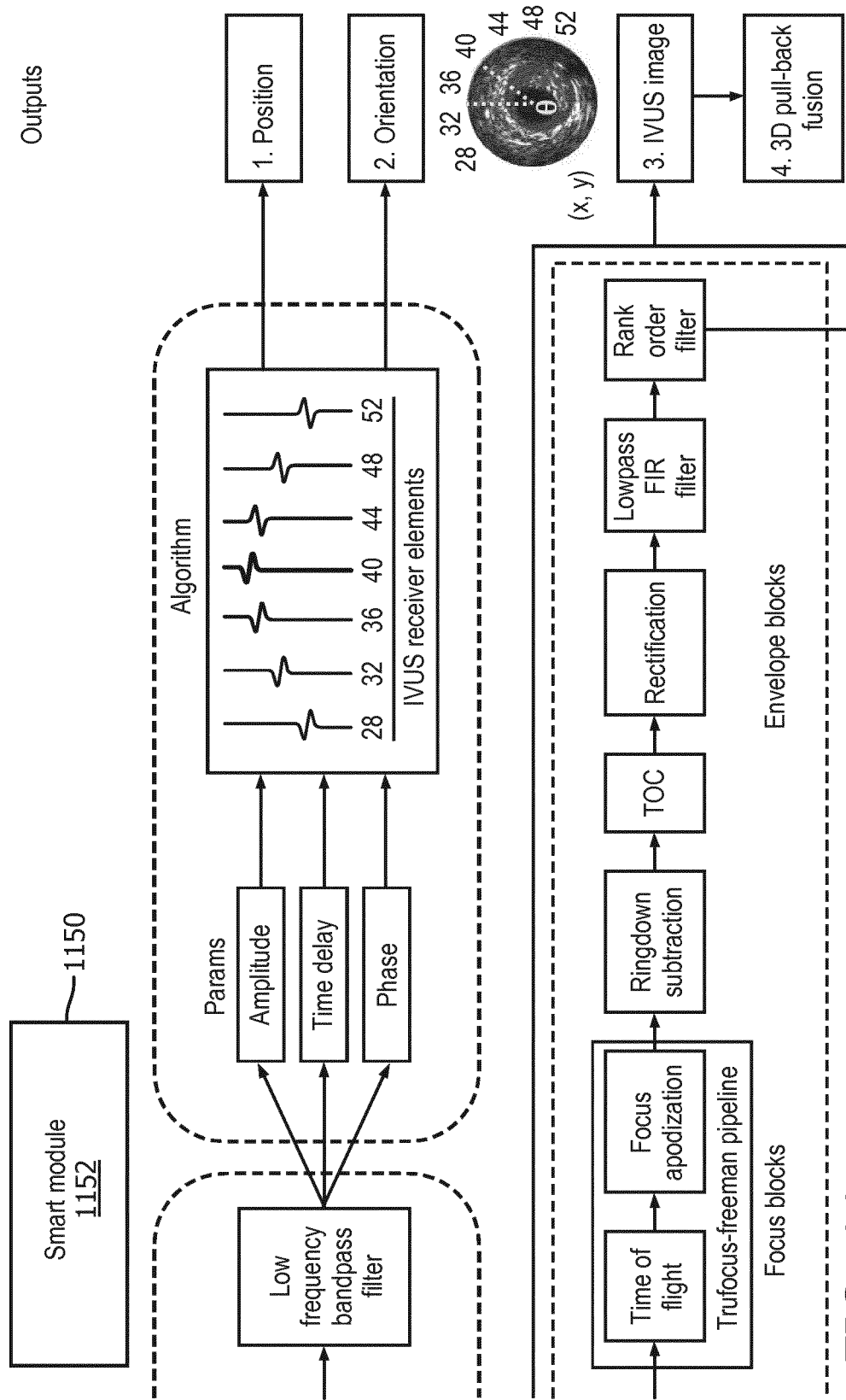
FIG. 11 (continue)

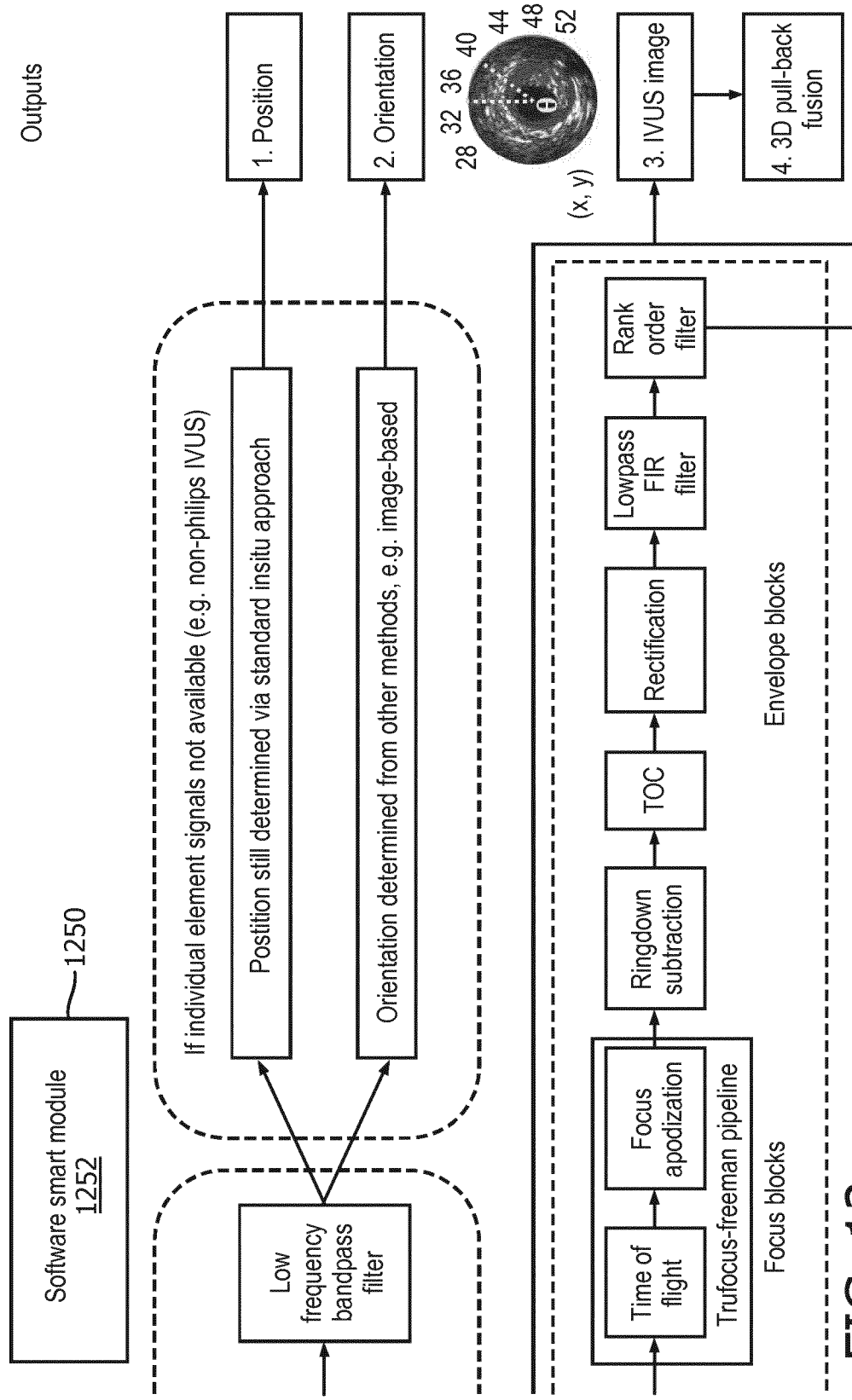
FIG. 12 (continue)

INTRAVASCULAR ULTRASOUND POSITION IDENTIFICATION

CROSS-REFERENCE TO PRIOR APPLICATIONS

This application is the U.S. National Phase application under 35 U.S.C. § 371 of International Application No. PCT/EP2019/065794, filed on Jun. 17, 2019, which claims the benefit of U.S. Provisional Patent Application No. 62/688,431, filed on Jun. 22, 2018. These applications are hereby incorporated by reference herein.

BACKGROUND

Interventional medical devices such as catheters are tracked using external ultrasound probes that transmit beams to passive ultrasound sensors (e.g., PZT, PVDF, copolymer or other piezoelectric material) on or in the interventional medical devices. The passive ultrasound sensor passively listens to the ultrasound waves incident on it as the external ultrasound probe's beams sweep the field of view of a diagnostic ultrasound B-mode imaging field. Analysis of the resultant signals yields the position of the passive ultrasound sensor on the interventional medical device in the frame of reference of the ultrasound image. The position can then be overlaid on the ultrasound image for enhanced visualization of the interventional medical device, and the positions and their histories can be logged for tracking, segmentation, and other applications. The tracking described above, known as 'InSitu' based tracking, is used to track the position and movement of the catheter or other interventional device.

Separately, an intravascular ultrasound (IVUS) probe can be moved (e.g., pushed and/or pulled) through a catheter to record ultrasound imagery in a small field-of-view from within a vessel. Currently, pullbacks of the intravascular ultrasound probe are assumed to be in a straight line, pulled at a constant speed. Due to the small field-of-view, the intravascular ultrasound imagery can be hard to interpret.

FIG. 1 illustrates a known system for tracking an interventional medical device using a passive ultrasound sensor. In FIG. 1, an ultrasound probe 102 emits an imaging beam 103 that sweeps across a passive ultrasound sensor 104 on a tool tip of an interventional medical device 105. Here, the ultrasound probe 102 is representative of the external ultrasound probe, and the interventional medical device 105 may be the catheter as compared to the intravascular ultrasound probe that moves within the catheter. An image of tissue 107 is fed back by the ultrasound probe 102. A location of the passive ultrasound sensor 104 on the tool tip of the interventional medical device 105 is provided as a tip location 108 upon determination by a signal processing algorithm. The tip location 108 is overlaid on the image of tissue 107 as an overlay image 109. The image of tissue 107, the tip location 108, and the overlay image 109 are all displayed on a display 100.

SUMMARY

According to an aspect of the present disclosure, a controller for identifying positioning of an intravascular ultrasound probe includes a memory that stores instructions and a processor that executes the instructions. When executed by the processor, the instructions cause the controller to execute a process that includes receiving first signals from at least one element of the intravascular ultrasound probe and receiving second signals from an external ultrasound probe. The processor determines, based on the first signals and the second signals, a position of the intravascular ultrasound probe in a tracking space that includes the intravascular ultrasound probe and the external ultrasound probe.

According to another aspect of the present disclosure, a method for identifying positioning of an intravascular ultrasound probe includes receiving, by a controller that includes a memory that stores instructions and a processor that executes the instructions, first signals from at least one element of the intravascular ultrasound probe and second signals from an external ultrasound probe. The controller determines, based on the first signals and the second signals, a position of the intravascular ultrasound probe in a tracking space that includes the intravascular ultrasound probe and the external ultrasound probe.

According to still another aspect of the present disclosure, a system for identifying positioning of an intravascular ultrasound probe includes the intravascular ultrasound probe, an external ultrasound probe, and a controller with a memory that stores instructions and a processor that executes the instructions. When executed by the processor, the instructions cause the controller to execute a process that includes receiving first signals from at least one element of the intravascular ultrasound probe and receiving second signals from an external ultrasound probe. The controller determines a position of the intravascular ultrasound probe in a tracking space that includes the intravascular ultrasound probe and the external ultrasound probe.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
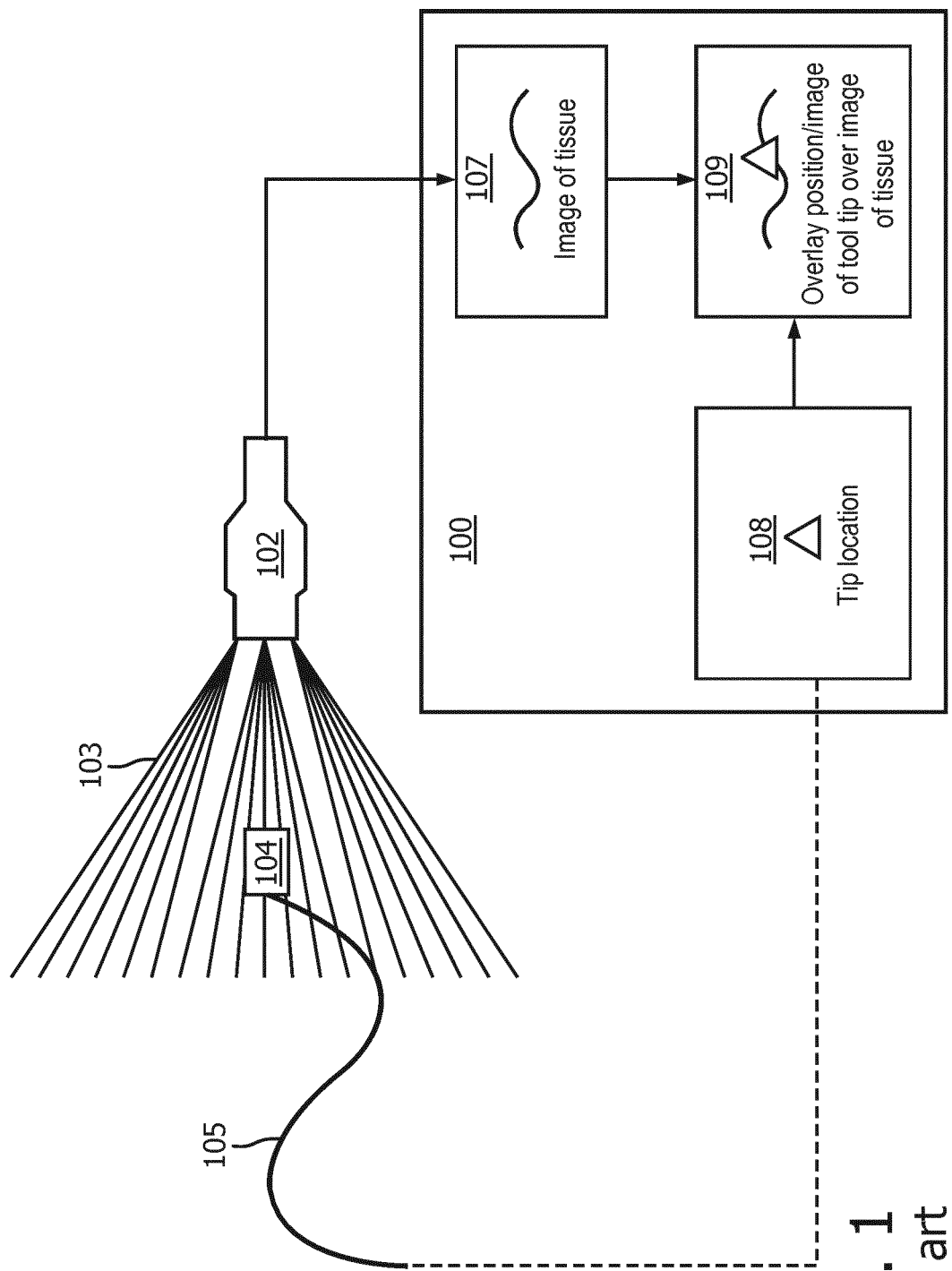
FIG. 1 illustrates a known system for intravascular ultrasound position identification using a passive ultrasound sensor, in accordance with a representative embodiment.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only, and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

Figure 2:
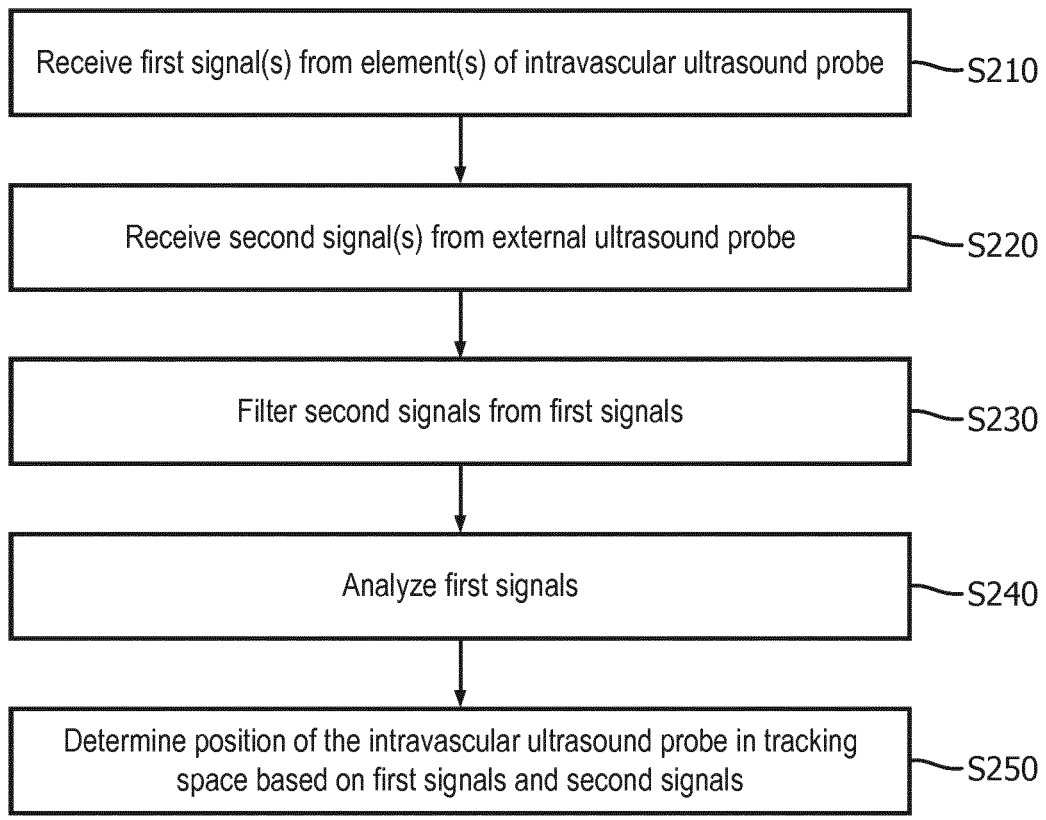
FIG. 2 illustrates a method for intravascular ultrasound position identification, in accordance with a representative embodiment.

FIG. 2 illustrates a method for intravascular ultrasound position identification, in accordance with a representative embodiment.

In FIG. 2, the process starts at S210 by receiving a first signal or signals from an element or elements of an intravascular ultrasound probe. The first signal or signals are based on the intravascular ultrasound probe emitting ultrasound waves within a vessel, such as to image the walls of the vessel. The ultrasound waves sweep the field of view of a diagnostic ultrasound B-mode imaging field, and reflections or backscatter are used to produce ultrasound imagery such as imagery of the walls of the vessel. The first signals are based on the ultrasound imagery produced from the reflections or backscatter. The first signals may be sent from an imaging element or array of elements on the intravascular ultrasound probe to a controller. A controller is explained below, but in summary includes at least a hardware module, and may detachably interface with a system that includes the intravascular ultrasound probe. The system that includes the intravascular ultrasound probe may include what is known as a patient interface module, which is a physical output (e.g., port) for outputting information from the intravascular ultrasound probe.

At S220, a second signal or signals is received from an element or elements of an external ultrasound probe (i.e., as distinguished from the intravascular ultrasound probe). The second signal or signals are based on the external ultrasound probe emitting ultrasound waves external to the vessel, and possibly external to the body of the human that contains the vessel. The ultrasound waves sweep the field of view of a diagnostic ultrasound B-mode imaging field, and reflections or backscatter are used to produce ultrasound imagery such as imagery tissue, bones, vessels and other parts of the human. The second signals are based on the ultrasound imagery produced from the reflections or backscatter. In embodiments described herein, the intravascular ultrasound probe within the vessel may be within the view of view of the external ultrasound probe, such that the intravascular ultrasound probe may be visible from the reflections of the imaging field emitted by the external ultrasound probe. An external ultrasound probe may be a handheld ultrasound probe that operates similar to the intravascular ultrasound probe, except that the external ultrasound probe is typically external to the body and is used typically to image a larger area or 3-dimensional ultrasound volume than the intravascular ultrasound probe. However, the external ultrasound probe may also be placed in a cavity within the body, for example in the case of transthoracic, transesophageal, or endobronchial ultrasound imaging. Nevertheless, the external probe is typically emitting ultrasound waves external to the vessel. The second signals are based on the ultrasound imagery produced from the reflections. The second signals may be sent from an imaging element or array of elements on the external ultrasound probe to the same controller that receives the first signals. As noted previously, a controller will be explained below.

At S230, second signals from the external ultrasound probe are filtered from the first signals from the intravascular ultrasound probe. The second filters may be filtered from the first signals by an analog filter, such as when the external ultrasound probe and intravascular ultrasound probe operate in different bandwidths of the frequency spectrum. The filtering at S230 may be performed by a filter intermediate to (between) the controller and the intravascular ultrasound probe and external ultrasound probe. Alternatively, the filtering at S230 may be performed by an analog filter circuit in the controller.

At S240, the first signals are analyzed. For example, the first signals may be analyzed to obtain the ultrasound imaging of the interior of the vessel. When the first signals are repeatedly received, such as when the intravascular ultrasound probe repeatedly emits an imaging field within the vessel in what is essentially a 2-dimensional circumference, multiple sequential captures of the 2-dimensional circumference may be aligned in order to create a 3-dimensional ultrasound volume.

At S250, the position of the intravascular ultrasound probe in a tracking space is determined based on the first signals and the second signals. A tracking space may be an overall 3-dimensional space with a predetermined/preset origin and that includes both the external ultrasound probe and the intravascular ultrasound probe. The position of the intravascular ultrasound probe may be determined from the second signals, such as when the intravascular ultrasound probe is captured in the ultrasound images from the external ultrasound probe. However, intravascular ultrasound position identification as described herein is primarily based on the first signals, explained below.

Figure 3:
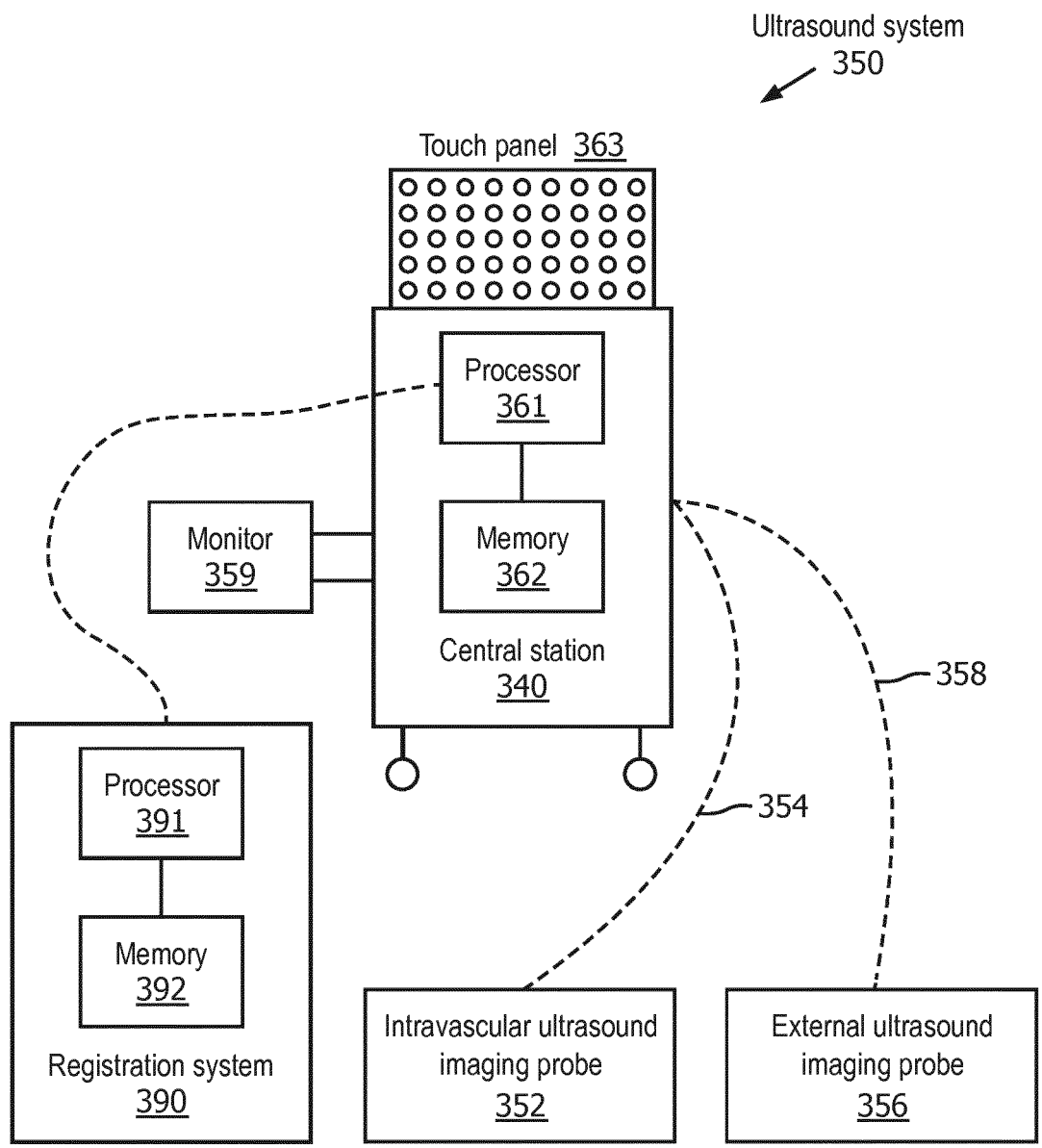
FIG. 3 illustrates a system for intravascular ultrasound position identification, in accordance with a representative embodiment.

FIG. 3 illustrates a system for intravascular ultrasound position identification, in accordance with a representative embodiment.

In FIG. 3, an ultrasound system 350 includes a central station 340 with a processor 361 and memory 362, a touch panel 363, a monitor 359, an external ultrasound imaging probe 356 connected to the central station 340 by a data connection 358 (e.g., a wired or wireless data connection), and an intravascular ultrasound imaging probe 352 connected to the central station 340 by a data connection 354 (e.g., a wired or wireless data connection). A registration system 390 includes a memory 392 that stores instructions and a processor 391 that executes the instructions. The registration system 390 is provided to register ultrasound imagery from the intravascular ultrasound imaging probe 352 to ultrasound imagery from the external ultrasound imaging probe 356.

A "controller" as described herein, may be implemented by at least the processor 361 and memory 362 in the central station 340, or by the processor 391 and memory 392 in the registration system 390. As noted previously, a controller may also include at least a hardware module, and may detachably interface with a system that includes the intravascular ultrasound imaging probe 352. The system that includes the intravascular ultrasound imaging probe 352 may include what is known as a patient interface module, which is a physical output (e.g., port) for outputting information from the intravascular ultrasound imaging probe 352 to, e.g., a controller via the hardware module.

The intravascular ultrasound imaging probe 352 may be provided at the end of a wire or similar instrument that is inserted through a catheter. The intravascular ultrasound imaging probe 352 produces ultrasound imagery resultant in the first signals described herein, and the external ultrasound imaging probe 356 produces ultrasound imagery resultant in the second signals described herein.

More particularly, in the embodiment of FIG. 3, each individual PZT element on/in an intravascular ultrasound imaging probe 352 sends the first signals as described herein. Time-of-flight measurements provide the axial/radial distance of each PZT element (passive ultrasound element) of the intravascular ultrasound imaging probe 352 from the external ultrasound imaging probe 356. Amplitude measurements and knowledge of the beam firing sequence may provide the lateral position of each PZT element. Since phase can correspond to time-of-flight, phase may be used instead of time-of-flight insofar as phase may provide higher measurement precision.

When multiple PZT elements are provided, the measurements can be averaged to provide an overall position of the intravascular ultrasound imaging probe 352. However, since relative positional arrangements of the PZT elements are known, the overall relative pose of the intravascular ultrasound imaging probe 352 can also be determined from the relative measurements of the first signals. For example, the PZT element facing the top or closest to facing the top should provide the strongest signal since it should be closest to the external ultrasound imaging probe 356.

As described above, when multiple PZT elements are provided in an intravascular ultrasound imaging probe 352, such as in an array, an average (overall) position of the intravascular ultrasound imaging probe 352 can be determined. Moreover, a pose of the intravascular ultrasound imaging probe 352 can also be determined, based on the first signals and the second signals, and particularly based on relative positions of the multiple PZT elements.

By way of explanation, the intravascular ultrasound imaging probe 352 is placed internally into a patient during a medical procedure. Locations of the intravascular ultrasound imaging probe 352 can be seen on imagery generated by the external ultrasound imaging probe 356. As described herein, second signals from the external ultrasound imaging probe 356 can also be used to detect a position of the intravascular ultrasound imaging probe 352. That is, second signals may include or reflect the beam firing sequence of beams fired by the external ultrasound imaging probe 356, and may provide context for the first signals from the intravascular ultrasound imaging probe 352.

Figure 4A:
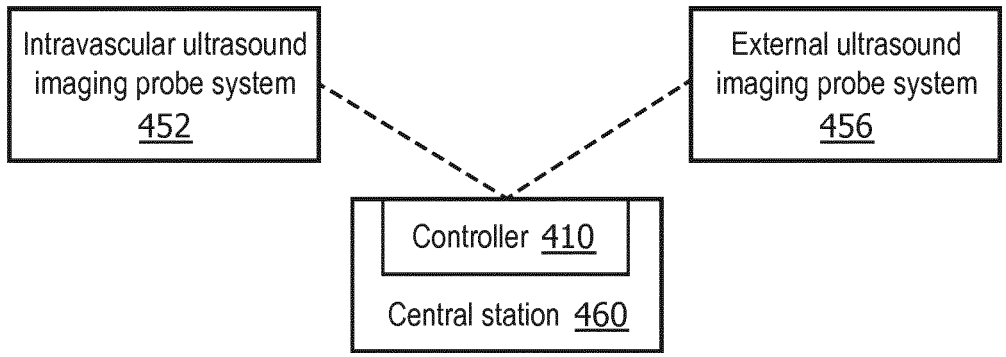
FIG. 4A illustrates a relationship between a controller and a system for intravascular ultrasound position identification, in accordance with a representative embodiment.

FIG. 4A illustrates a relationship between a controller and a system for intravascular ultrasound position identification, in accordance with a representative embodiment.

In the embodiment of FIG. 4A, a controller 410 is provided on or in a central station 460. The controller 410 receives first signals from the intravascular ultrasound imaging probe system 452, and second signals from the external ultrasound imaging probe system 456. The intravascular ultrasound imaging probe system 452 may be an overall system that includes an intravascular ultrasound imaging probe 352 along with other elements such as an interface. The external ultrasound imaging probe system 456 may be an overall system that includes an external ultrasound imaging probe 356 along with other elements such as an interface.

Figure 4B:
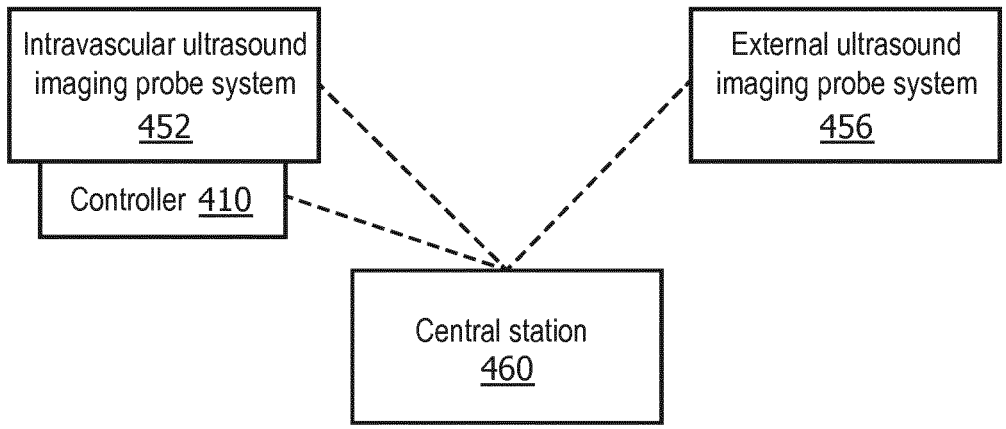
FIG. 4B illustrates a relationship between a controller and a system for intravascular ultrasound position identification, in accordance with a representative embodiment.

FIG. 4B illustrates a relationship between a controller and a system for intravascular ultrasound position identification, in accordance with a representative embodiment.

In the embodiment of FIG. 4b, the controller 410 is provided on or in the intravascular ultrasound imaging probe system 452 rather than on or in the central station 460. The controller 410 obtains the first signals from other components of the intravascular ultrasound imaging probe system 452, and receives the second signals from the external ultrasound imaging probe system 456 via the central station 460.

Figure 4C:
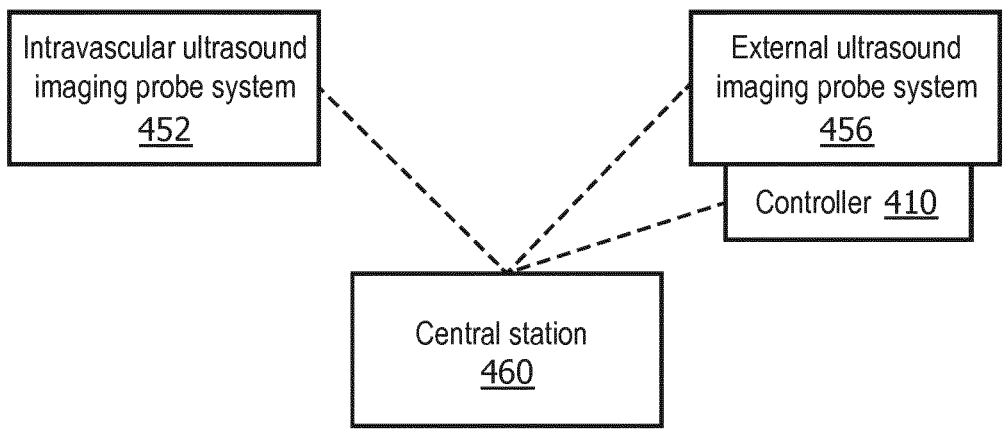
FIG. 4C illustrates a relationship between a controller and a system for intravascular ultrasound position identification, in accordance with a representative embodiment.

FIG. 4C illustrates a relationship between a controller and a system for intravascular ultrasound position identification, in accordance with a representative embodiment.

In the embodiment of FIG. 4C, the controller 410 is provided on or in the external ultrasound imaging probe system 456, rather than on or in the central station 460 or the intravascular ultrasound imaging probe system 452. The controller 410 obtains the first signals from other components of the external ultrasound imaging probe system 456, and receives the first signals from the intravascular ultrasound imaging probe system 452 via the central station 460.

Figure 5:
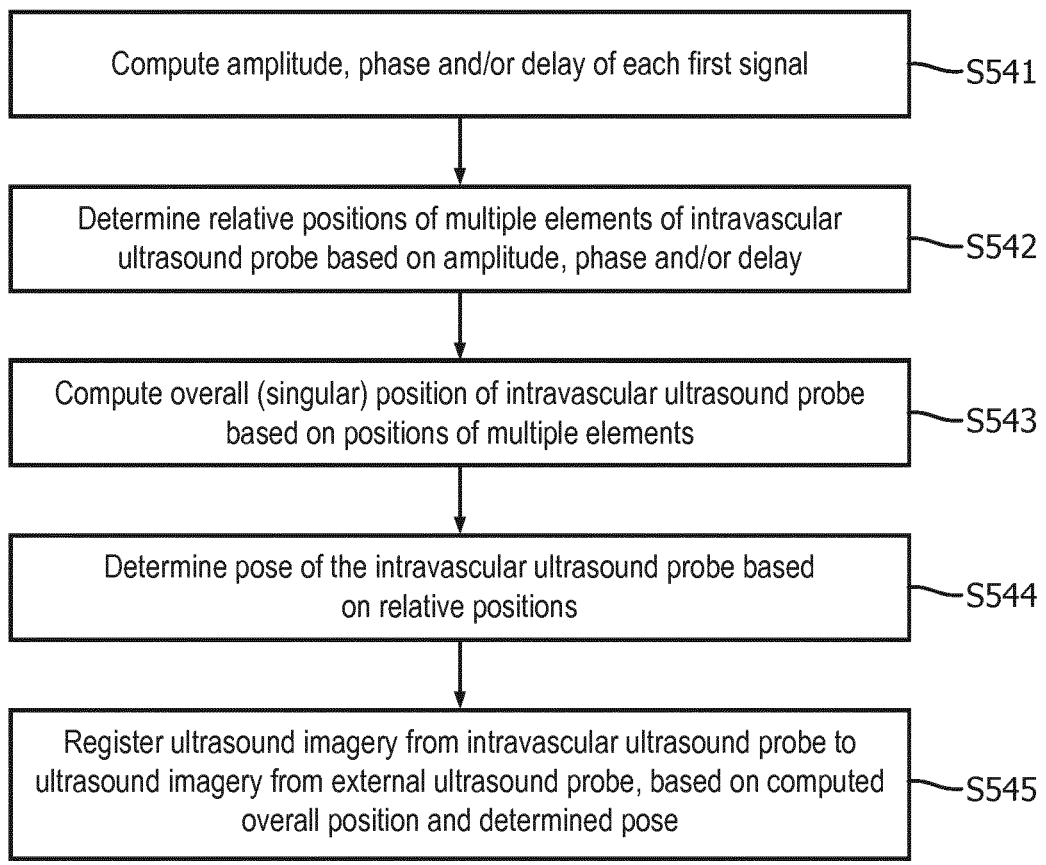
FIG. 5 illustrates another method for intravascular ultrasound position identification, in accordance with a representative embodiment.

FIG. 5 illustrates another method for intravascular ultrasound position identification, in accordance with a representative embodiment.

In FIG. 5, the process starts at S541 with computing an amplitude, a phase, and/or a delay of each first signal received from an intravascular ultrasound imaging probe 352. The amplitude, phase, and delay vary for each element due to each element being in different positions, and the positions of the elements in/on the intravascular ultrasound imaging probe 352 are thus determined based on differential characteristics of each of the elements. Each first signal includes information representative of both absolute and relative positions of the intravascular ultrasound imaging probe 352. At S542, relative positions of multiple elements of the intravascular ultrasound probe are determined based on the amplitude, phase and/or delay of each first signal.

At S543, an overall (singular) position of the intravascular ultrasound imaging probe 352 is computed based on positions of multiple elements of the intravascular ultrasound imaging probe 352. That is, first signals based on positions of multiple elements of the intravascular ultrasound imaging probe 352 can be used to compute one and only one position as an overall position of the intravascular ultrasound imaging probe 352. For example, an average of the time-of-flight measurements may be used to provide the axial/radial distance of the intravascular ultrasound imaging probe 352 overall. An average of the amplitude measurements may be used to provide lateral position of the intravascular ultrasound imaging probe 352 overall. As noted previously, phase may be used in lieu of time-of-flight insofar as phase may provide higher measurement precision.

At S544, a pose of the intravascular ultrasound imaging probe 352 is determined based on relative positions. That is, the individual signals may be comparatively used to determine which element is in each of predetermined positions in an arrangement of the elements in/on the intravascular ultrasound imaging probe 352. For example, and as noted previously, the strongest signal should be from the element at the top (closest to, and facing) the external ultrasound imaging probe 356. Decreased strength in received signals should correspond to relatively greater distances and angles from the external ultrasound imaging probe 356.

At S545, ultrasound imagery from the intravascular ultrasound imaging probe 352 is registered to ultrasound imagery from the external ultrasound imaging probe 356, based on the computed overall position from S543 and the determined pose from S544. That is, intravascular imagery captured by the intravascular ultrasound imaging probe 352 may be registered by aligning precisely the features of the intravascular ultrasound imagery to features of the external ultrasound imagery. As a reminder, the external ultrasound imagery captured by the external ultrasound imaging probe 356 may include the intravascular ultrasound imaging probe 352.

Figure 6:
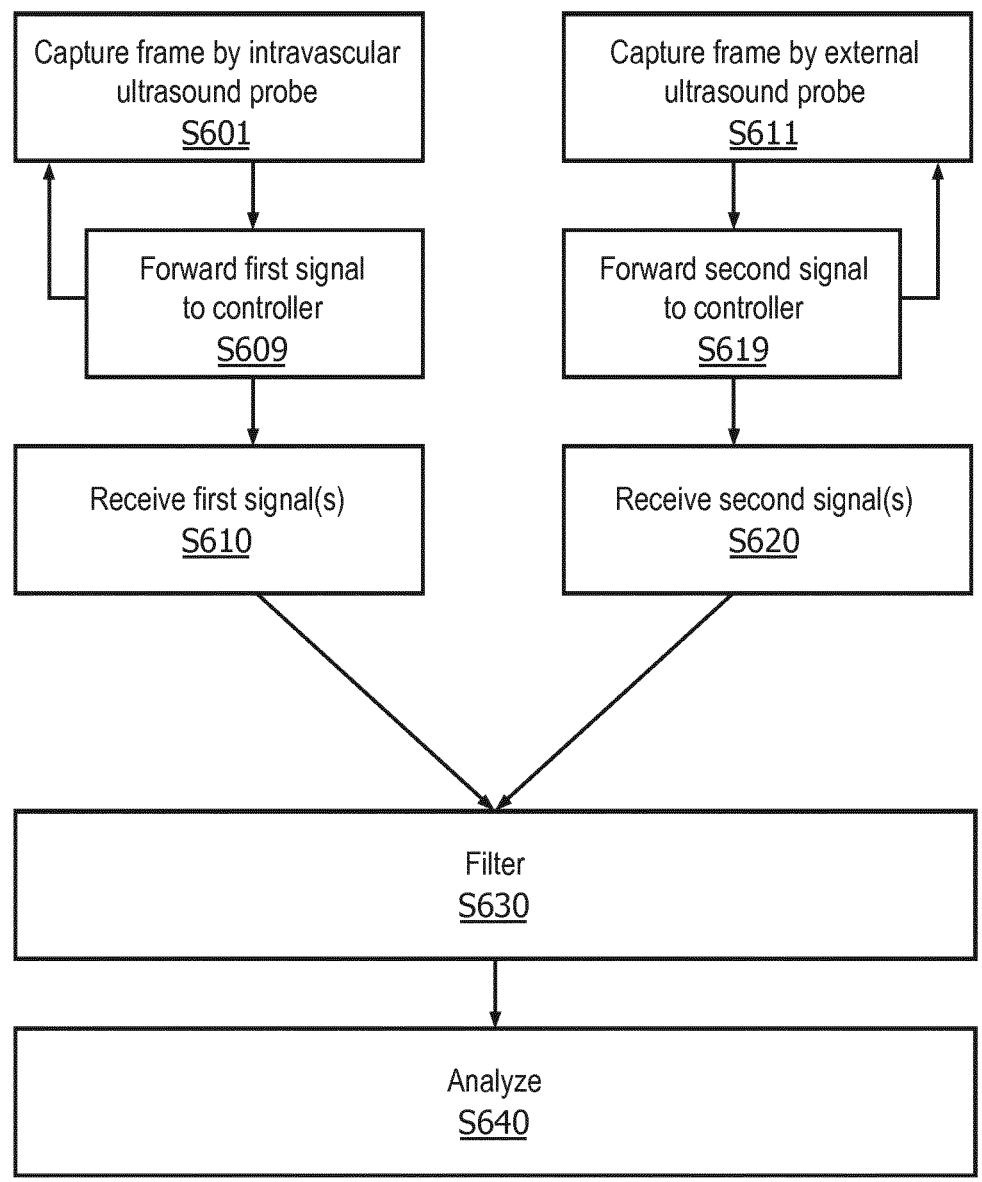
FIG. 6 illustrates another method for intravascular ultrasound position identification, in accordance with a representative embodiment.

FIG. 6 illustrates another method for intravascular ultrasound position identification, in accordance with a representative embodiment.

In FIG. 6, a process involving the intravascular ultrasound imaging probe 352 is initially separated from a process involving the external ultrasound imaging probe 356. The processes may be performed simultaneously. In other words, first signals and second signals may be alternately processed based on simultaneous or near-simultaneous (e.g., overlapping) captures of frames by the intravascular ultrasound imaging probe 352 and the external ultrasound imaging probe 356.

That is, at S601, a frame is captured by the intravascular ultrasound imaging probe 352. The first signal is then forwarded to the controller 310 at S609, and the process both returns to S601 as a loop to result in capturing the next frame, but also proceeds to S610 where the first signals are received by the controller 310.

Simultaneous with the process from S601 to S610, a frame is captured by the external ultrasound imaging probe 356 at S611. The second signal is then forwarded to the controller 310 at S619, and the process both returns to S611 as a loop to result in capturing the next frame, but also proceeds to S620 where the second signals are received by the controller 310. The processes from S601 to S610 and from S6100 to S620 do not have to be performed exactly simultaneously. Rather, the relative timing of these processes merely reflects that the frame captures and forwarding of first signals and second signals are not necessarily alternated.

At S630, analog filtering is provided to, for example, isolate the first signals. The filtering at S630 may be non-destructive, in that the second signals may still be provided for processing, such as to identify the timing of the beam firing sequence and/or to process ultrasound imagery from the external ultrasound imaging probe 356.

At S640, the first signals are analyzed. The analysis at S640 may be performed to identify the overall position of the intravascular ultrasound imaging probe 352, the individual positions of each element in/on the intravascular ultrasound imaging probe 352, and/or the pose of the intravascular ultrasound imaging probe 352 (based on individual relative positions of each element).

Figure 7:
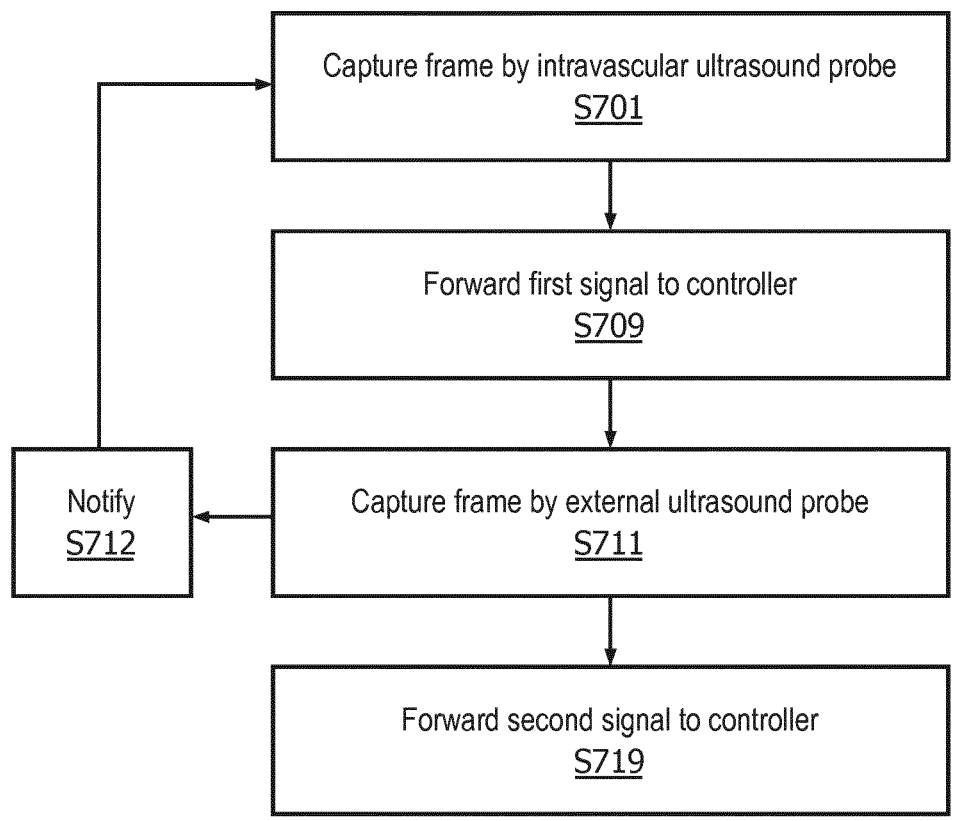
FIG. 7 illustrates another method for intravascular ultrasound position identification, in accordance with a representative embodiment.

FIG. 7 illustrates another method for intravascular ultrasound position identification, in accordance with a representative embodiment.

In FIG. 7, a process involving the intravascular ultrasound imaging probe 352 is initially alternated with a process involving the external ultrasound imaging probe 356. The processes may be synchronized by a common clock and/or by active instructions and control from the controller 310.

That is, at S701, a frame is captured by the intravascular ultrasound imaging probe 352. The first signal is then forwarded to the controller 310 at S709. At S711, a frame is captured by the external ultrasound imaging probe 356. At S712, the intravascular ultrasound imaging probe 352 may be actively notified of the frame capture by the external ultrasound imaging probe 356, such as to notify the intravascular ultrasound imaging probe 352 of its turn to capture the next frame. At S719, the second signal is forwarded to the controller 310. In other words, first signals and second signals are alternately processed based on alternative captures of frames by the intravascular ultrasound imaging probe 352 and the external ultrasound imaging probe 356.

Subsequent processing in the embodiment of FIG. 7 may be the same as in FIG. 6, and may involve analog filtering to isolate the first signals, and analysis of the first signals. The analysis of the first signals will identify the amplitude, phase and/or delay from each element of the intravascular ultrasound imaging probe 352, to identify positions of each element and the pose of the intravascular ultrasound imaging probe 352 from relative positions of each element.

Figure 8:
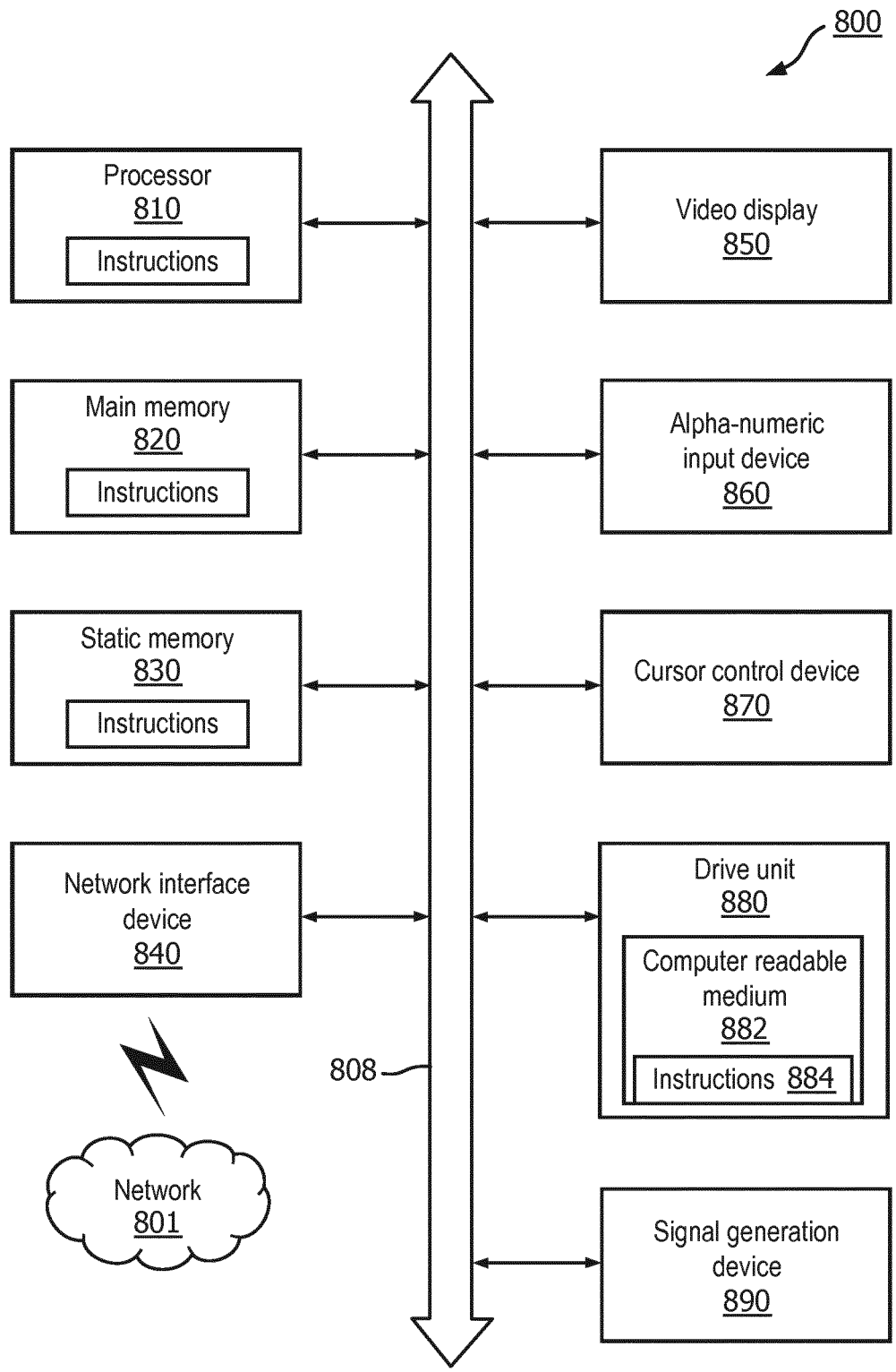
FIG. 8 is an illustrative embodiment of a general computer system, on which a method of intravascular ultrasound position identification can be implemented, in accordance with a representative embodiment.

FIG. 8 illustrates a general computer system, on which a method of intravascular ultrasound position identification can be implemented, in accordance with a representative embodiment.

The computer system 800 can include a set of instructions that can be executed to cause the computer system 800 to perform any one or more of the methods or computer based functions disclosed herein. The computer system 800 may operate as a standalone device or may be connected, for example, using a network 801, to other computer systems or peripheral devices. Any or all of the elements and characteristics of the computer system 800 in FIG. 8 may be representative of elements and characteristics of the central station 340, the registration system 390, the external ultrasound imaging probe 356, the intravascular ultrasound imaging probe 352, or other similar devices and systems that can include a controller and perform the processes described herein.

In a networked deployment, the computer system 800 may operate in the capacity of a client in a server-client user network environment. The computer system 800 can also be fully or partially implemented as or incorporated into various devices, such as a control station, imaging probe, passive ultrasound sensor, stationary computer, a mobile computer, a personal computer (PC), or any other machine capable of executing a set of instructions (sequential or otherwise) that specify actions to be taken by that machine. The computer system 800 can be incorporated as or in a device that in turn is in an integrated system that includes additional devices. In an embodiment, the computer system 800 can be implemented using electronic devices that provide video or data communication. Further, while the computer system 800 is illustrated, the term "system" shall also be taken to include any collection of systems or sub-systems that individually or jointly execute a set, or multiple sets, of instructions to perform one or more computer functions.

As illustrated in FIG. 8, the computer system 800 includes a processor 810. A processor 810 for a computer system 800 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. Any processor described herein is an article of manufacture and/or a machine component. A processor for a computer system 800 is configured to execute software instructions to perform functions as described in the various embodiments herein. A processor for a computer system 800 may be a general-purpose processor or may be part of an application specific integrated circuit (ASIC). A processor for a computer system 800 may also be a microprocessor, a microcomputer, a processor chip, a controller, a microcontroller, a digital signal processor (DSP), a state machine, or a programmable logic device. A processor for a computer system 800 may also be a logical circuit, including a programmable gate array (PGA) such as a field programmable gate array (FPGA), or another type of circuit that includes discrete gate and/or transistor logic. A processor for a computer system 800 may be a central processing unit (CPU), a graphics processing unit (GPU), or both. Additionally, any processor described herein may include multiple processors, parallel processors, or both. Multiple processors may be included in, or coupled to, a single device or multiple devices.

Moreover, the computer system 800 includes a main memory 820 and a static memory 830 that can communicate with each other via a bus 808. Memories described herein are tangible storage mediums that can store data and executable instructions, and are non-transitory during the time instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

As shown, the computer system 800 may further include a video display unit 850, such as a liquid crystal display (LCD), an organic light emitting diode (OLED), a flat panel display, a solid-state display, or a cathode ray tube (CRT). Additionally, the computer system 800 may include an input device 860, such as a keyboard/virtual keyboard or touch-sensitive input screen or speech input with speech recognition, and a cursor control device 870, such as a mouse or touch-sensitive input screen or pad. The computer system 800 can also include a disk drive unit 880, a signal generation device 890, such as a speaker or remote control, and a network interface device 840.

In an embodiment, as depicted in FIG. 8, the disk drive unit 880 may include a computer-readable medium 882 in which one or more sets of instructions 884, e.g. software, can be embedded. Sets of instructions 884 can be read from the computer-readable medium 882. Further, the instructions 884, when executed by a processor, can be used to perform one or more of the methods and processes as described herein. In an embodiment, the instructions 884 may reside completely, or at least partially, within the main memory 820, the static memory 830, and/or within the processor 810 during execution by the computer system 800.

In an alternative embodiment, dedicated hardware implementations, such as application-specific integrated circuits (ASICs), programmable logic arrays and other hardware components, can be constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionality as described herein, and a processor described herein may be used to support a virtual processing environment.

The present disclosure contemplates a computer-readable medium 882 that includes instructions 884 or receives and executes instructions 884 responsive to a propagated signal; so that a device connected to a network 801 can communicate video or data over the network 801. Further, the instructions 884 may be transmitted or received over the network 801 via the network interface device 840.

Figure 9:
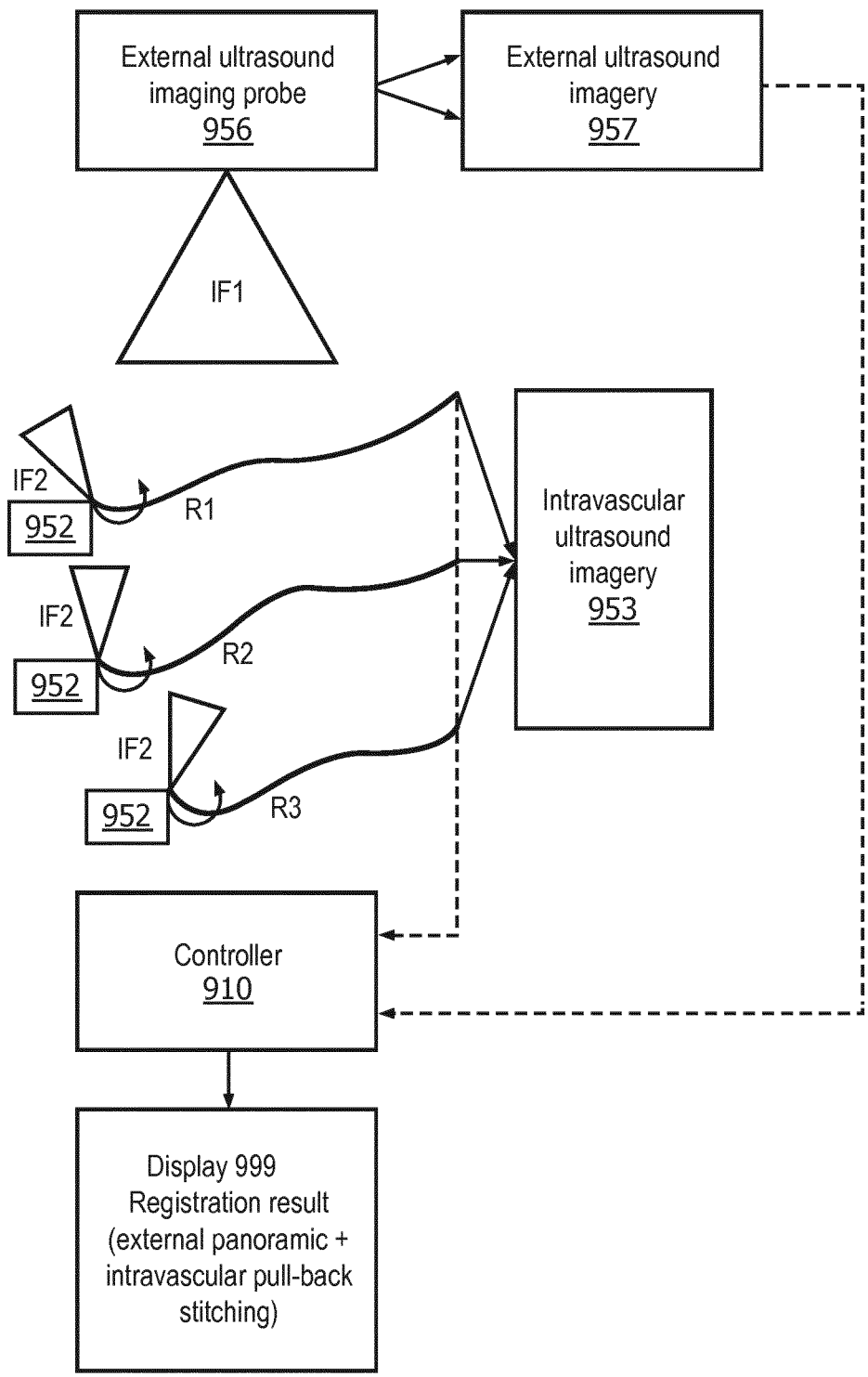
FIG. 9 illustrates a conceptual overview of a system and process for intravascular ultrasound position identification, in accordance with a representative embodiment.

FIG. 9 illustrates a conceptual overview of a system and process for intravascular ultrasound position identification, in accordance with a representative embodiment.

In FIG. 9, an external ultrasound imaging probe 956 corresponds to the external ultrasound imaging probe 356 described elsewhere herein. A first imaging field from the external ultrasound imaging probe 956 is designated IF1. The external ultrasound imaging probe 956 produces external ultrasound imagery 957 to a controller 910.

An intravascular ultrasound imaging probe 952 is shown within the imaging field IF1 of the external ultrasound imaging probe 956 as the intravascular ultrasound imaging probe 952 is pulled back. Rotations R1 to R3 reflect different rotations of the intravascular ultrasound imaging probe 952 during the pullback. The intravascular ultrasound imaging probe 952 produces intravascular ultrasound imagery 953. The controller produces a display 999 of a registration result. The registration result may include the external imagery from the external ultrasound imaging probe 956 and the intravascular ultrasound imagery 953 from the intravascular ultrasound imaging probe 952. The intravascular ultrasound imagery 953 may consist of individual images from the intravascular ultrasound probe 952 in a manner that is stitched together from the three different positions shown. In other words, the intravascular ultrasound imagery 953 represents a sequence of positions of the intravascular ultrasound imaging probe 952, and the external panoramic is a display of ultrasound images produced by the external ultrasound imaging probe 956. However, the registration as described may also be obtained when a pullback is not performed, for example when the intravascular ultrasound imaging probe 952 remains stationary within the first imaging field IF1.

Figure 10A:
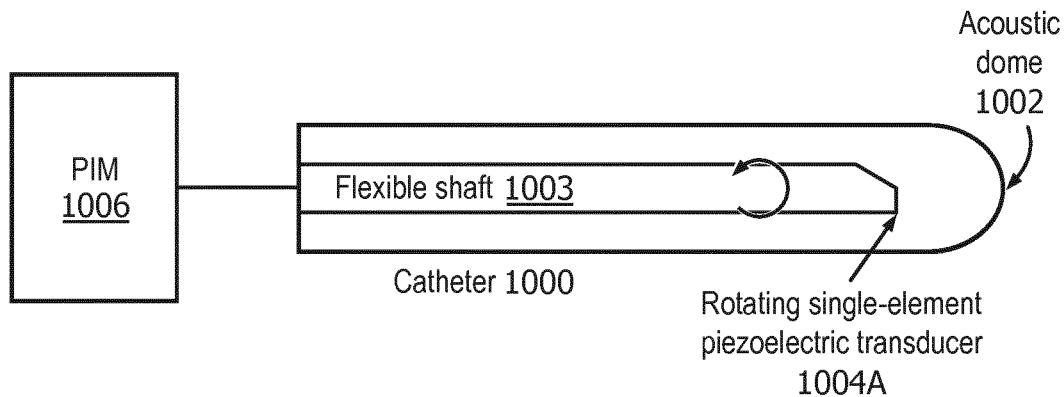
FIG. 10A illustrates a catheter with a single-element intravascular ultrasound probe used in intravascular ultrasound position identification, in accordance with a representative embodiment.

FIG. 10A illustrates a catheter with a single-element intravascular ultrasound probe used in intravascular ultrasound position identification, in accordance with a representative embodiment.

In FIG. 10A, a single-element rotates in an intravascular ultrasound imaging probe 352. A rotating single-element piezoelectric transducer 1004A is rotated by or about a flexible shaft 1003 in a catheter 1000 with an acoustic dome 1002. The rotating single-element piezoelectric transducer 1004A may be rotated about a circumference to receive signals from an external ultrasound imaging probe 356 in three hundred sixty (360°) degrees.

Figure 10B:
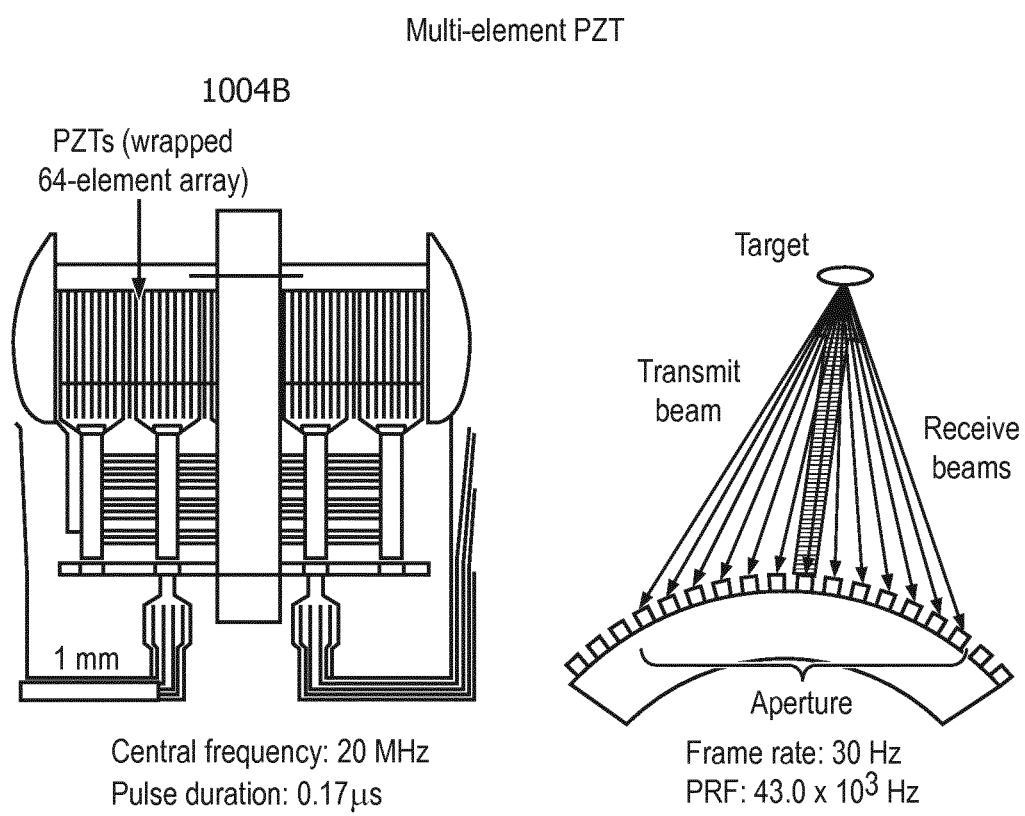
FIG. 10B illustrates a multi-element intravascular ultrasound probe used in intravascular ultrasound position identification, in accordance with a representative embodiment.

FIG. 10B illustrates a multi-element intravascular ultrasound probe used in intravascular ultrasound position identification, in accordance with a representative embodiment.

In FIG. 10B, 64 elements of an array are arranged at fixed positions around a circumference to receive signals from an external ultrasound imaging probe 356 in three hundred sixty (360°) degrees. The central frequency is 20 megahertz (MHz), and pulse duration of each received beam from the external ultrasound imaging probe 356 is 0.17 microseconds. On the right, a transmit beam is shown by the thickest line in the center that ends in the arrow. Receive beams are shown by the thinner lines between the target and the aperture. Here, the frame rate is 30 hertz (Hz), with a pulse repetition frequency (PRF) of 43000 hertz (Hz). This is one example of a phased array intravascular ultrasound probe; however, the described methods and embodiments are applicable to a wide range of intravascular ultrasound probe systems, settings, and configurations.

In the embodiments that follow, it will be clear that intravascular ultrasound position identification is possible with 2-dimensional or 3-dimensional systems, including external ultrasound imaging probes 356 with both 2-dimensional and 3-dimensional transducers. Intravascular ultrasound position identification, as described, is compatible with systems from multiple different manufacturers, and may require acquiring signals from one or more elements (i.e., fewer than all) of an intravascular ultrasound imaging probe 352 or the aggregate of all such elements. Acquiring orientation directly may require the signals from each element or at least multiple elements of the intravascular ultrasound imaging probe 352, regardless of manufacturer. The tracking can also be provided for 2-dimensional single element intravascular ultrasound probes, 2-dimensional phased-array intravascular ultrasound probes, and 3-dimensional phased array intravascular ultrasound probes. Moreover, tracking can be provided for both simultaneous and alternating frame capture by the intravascular ultrasound imaging probe 352 and external ultrasound imaging probe 356.

Figure 11:
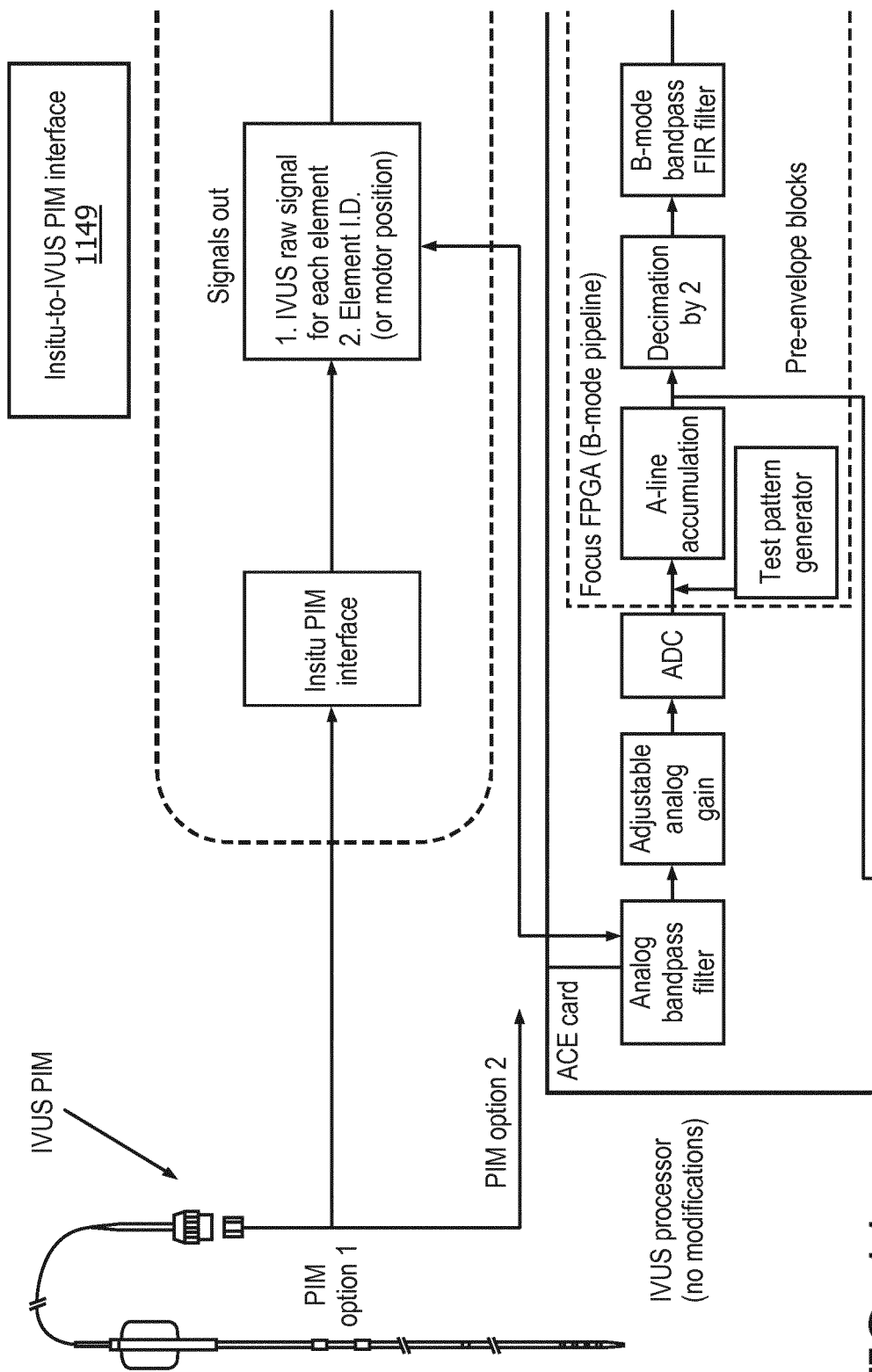
FIG. 11 illustrates a schematic overview for registration of intravascular ultrasound imagery to external ultrasound imagery in intravascular ultrasound position identification.

FIG. 11 illustrates a schematic overview for registration of intravascular ultrasound imagery to external ultrasound imagery in intravascular ultrasound position identification.

In the embodiment of FIG. 11 and other embodiments, a hardware module 1150 is provided as an interface between an InSitu system and the intravascular ultrasound imaging probe 352. Analog and digital signal processing software modules are provided for analog filtering, image processing and so on. In FIG. 11, these software modules are referred to as the smart module 1152.

The hardware module 1150 interfaces with an existing connection 1149 on/at a patient interface module on the intravascular ultrasound imaging probe 352, and retrieves the signal out from each element on the intravascular ultrasound imaging probe 352. The existing connection 1149 may be an interface between an InSitu system and the intravascular ultrasound imaging probe 352. An example of the existing connection 1149 is an InSitu console that connects with a console for the intravascular ultrasound imaging probe 352. The existing connection 1149 may provide compatibility for equipment from different manufacturers. In an embodiment, the existing connection 1149 allows for retrieval of a signal from each element of the intravascular ultrasound imaging probe 352.

The smart module 1152 may be or include software that then processes the received signal streams, extracts relevant information such as signal amplitude, phase, time delay, and uses the data to compute the relative position and orientation of each element. The smart module 1152 then determines the pose of the intravascular ultrasound imaging probe 352 based on the relative pose of the individual elements. Using the elements described for FIG. 11, no modifications may be necessary for transducers of an existing intravascular ultrasound imaging probe 352 or external ultrasound imaging probe 356.

Figure 12:
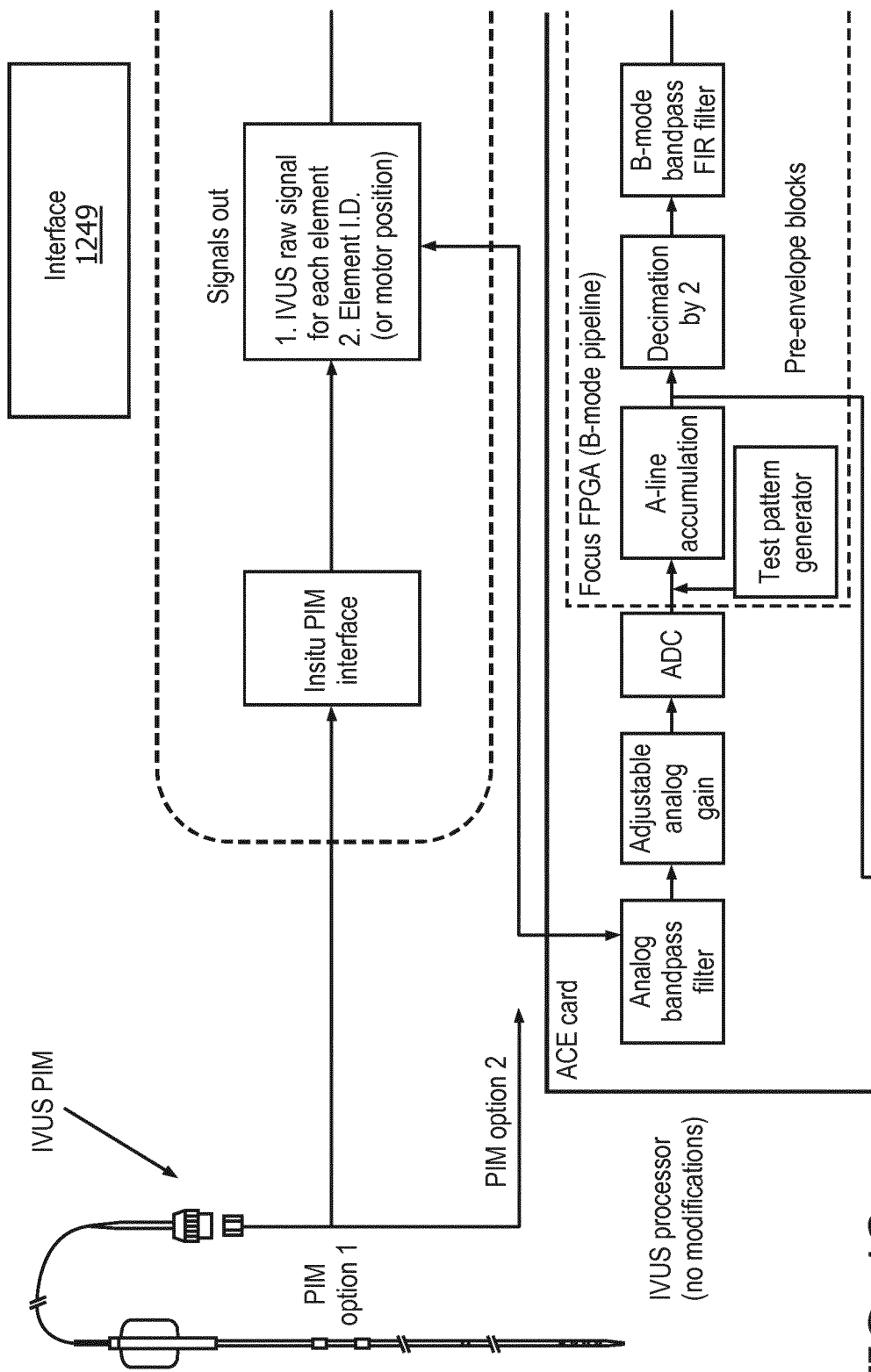
FIG. 12 illustrates a schematic for registration of intravascular ultrasound imagery to external ultrasound imagery in intravascular ultrasound position identification, in accordance with a representative embodiment.

FIG. 12 illustrates a schematic for registration of intravascular ultrasound imagery to external ultrasound imagery in intravascular ultrasound position identification, in accordance with a representative embodiment.

In an embodiment of FIG. 12, signals from individual elements of an intravascular ultrasound imaging probe 352 cannot be retrieved. Here, position can still be determined by considering an overall (aggregate) signal from the sensor elements of the intravascular ultrasound imaging probe 352. Orientation can be determined such as based on image-based registration, or by fusion with secondary imaging modalities such as angiography or active tracking using sensors other than InSitu sensors. Image-based registration, when used, may follow an initial global orientation calibration.

More particularly, in the embodiment of FIG. 12, an interface is provided between InSitu sensors to the intravascular ultrasound imaging probe 352.

The hardware module 1250 interfaces with an existing connection 1249 on/at a patient interface module on the intravascular ultrasound imaging probe 352, and retrieves the signal out from each element on the intravascular ultrasound imaging probe 352. The existing connection 1249 may be an InSitu console that connects with a patient interface module of a system that includes the intravascular ultrasound imaging probe 352. An example of the existing connection 1249 is an InSitu console that connects with a console for the intravascular ultrasound imaging probe 352. The existing connection 1249 may provide compatibility for equipment from different manufacturers.

In an embodiment, the existing connection 1249 allows for retrieval of a signal from each element of the intravascular ultrasound imaging probe 352. Signals are retrieved from each element of the intravascular ultrasound imaging probe 352 when they are available. However, if the individual element signals are not available, the overall position of the intravascular ultrasound imaging probe 352 can still be determined from the elements. Orientation is simply determined from another available method, such as image-based registration. Position is still determined by the smart module 1252 in a hardware module 1250.

In the embodiments of FIGS. 13 to 17 that follow, intravascular ultrasound position identification can be used to indicate a position of an intravascular ultrasound imaging probe 352 as tracked by an external ultrasound imaging probe 356. Intravascular ultrasound position identification can also be used to correct orientation of an intravascular ultrasound imaging probe 352 when an external ultrasound imaging probe 356 is used. Intravascular ultrasound position identification will ultimately improve registration or fusion of image formation between ultrasound imagery from an intravascular ultrasound imaging probe 352 and an external ultrasound imaging probe 356. As should be clear, intravascular ultrasound position identification as described herein can be used to modify systems with existing intravascular ultrasound imaging probes 352, to extend functionality thereof.

Figure 13:
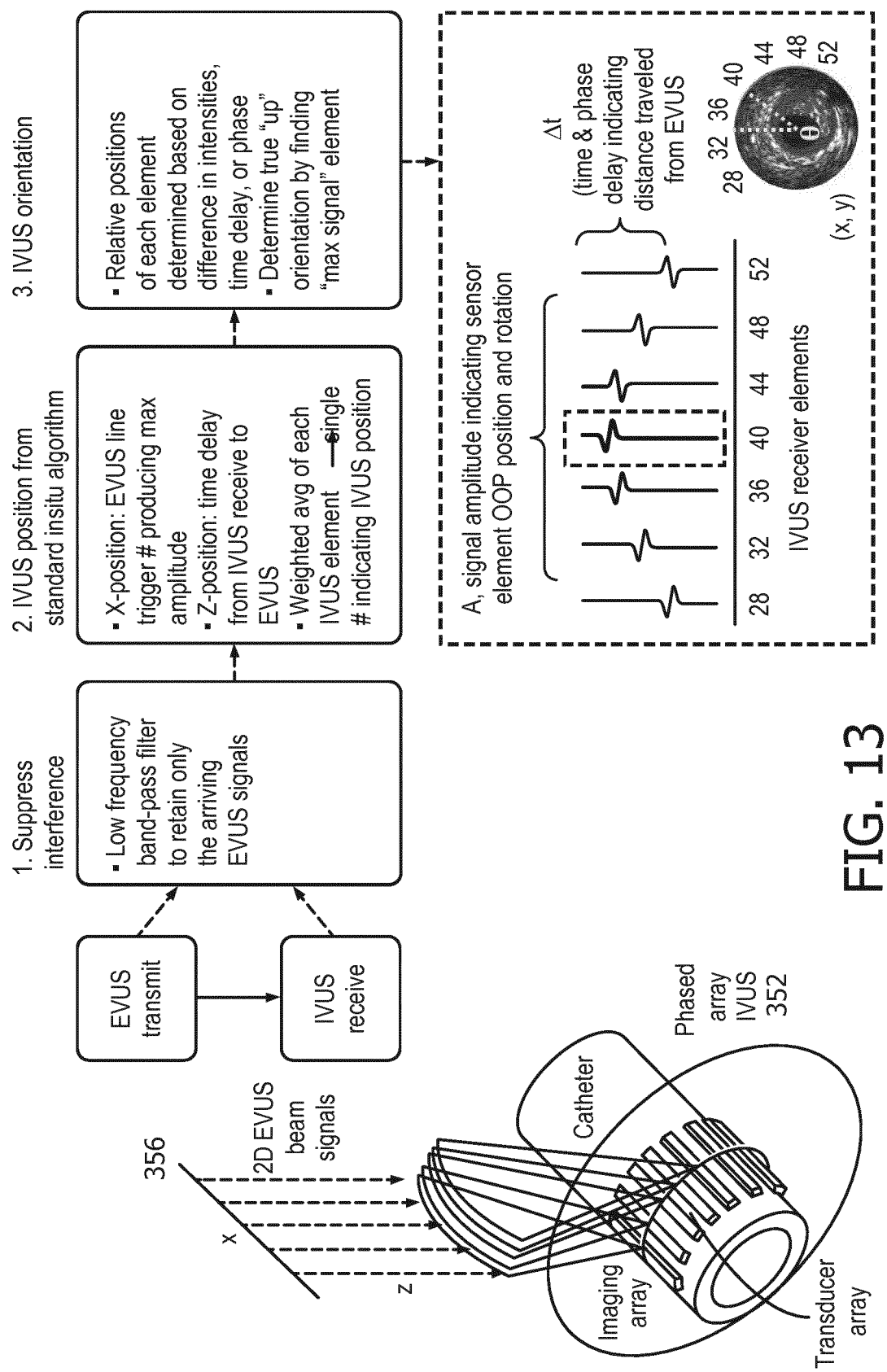
FIG. 13 illustrates a system with a phased array intravascular ultrasound and a 2-dimensional external ultrasound in intravascular ultrasound position identification, in accordance with a representative embodiment.

FIG. 13 illustrates a system with a phased array intravascular ultrasound and a 2-dimensional external ultrasound in intravascular ultrasound position identification, in accordance with a representative embodiment.

In the embodiment of FIG. 13, an intravascular ultrasound imaging probe 352 has a phased array of elements, and the external ultrasound imaging probe 356 produces a 2-dimensional imaging field. In this embodiment, the X-position of each element of the intravascular ultrasound imaging probe 352 is determined by the line trigger of the external ultrasound imaging probe 356 producing the maximum signal amplitude, while the Z-position is determined by the time-of-flight between the transmit of the external ultrasound imaging probe 356 and the receive of the intravascular ultrasound imaging probe 352. The 'centroid' of the position of each element of the array of the intravascular ultrasound imaging probe 352 then corresponds to the overall position of the intravascular ultrasound imaging probe 352. Rotation is computed based on the relative positions of each element, with the "up" direction corresponding to the element(s) of the intravascular ultrasound imaging probe 352 with maximum signal amplitude/minimum time delay, which in turn corresponds to the element(s) of the intravascular ultrasound imaging probe that face the external ultrasound imaging probe.

In the embodiment of FIG. 13, an intravascular ultrasound imaging probe 352 includes a phased array of elements. More particularly, multiple elements correspond to a predetermined configuration in/on the intravascular ultrasound imaging probe 352 (for example a fixed angular distance between each element), and the external ultrasound imaging probe 356 is used to identify the relative locations of the multiple elements. The multiple elements are relatively fixed in place so as to repeatedly emit ultrasound beams and record reflected responses. Additionally, the multiple elements each include a passive ultrasound sensor that receives and reflects signals from the external ultrasound imaging probe 356. As an example, the multiple elements may be arranged in 36 positions each ten (10) degrees apart, so as to repeatedly emit ultrasound beams and record reflected responses In the embodiment of FIG. 13, a 2-dimensional external ultrasound imaging probe 356 is used. A low pass filter is used to retain the low frequency signals arriving at the external ultrasound imaging probe 356. An X position of the intravascular ultrasound imaging probe 352 is determined based on identifying which line trigger of the external ultrasound imaging probe 356 produces the maximum amplitude in a received signal on the intravascular ultrasound imaging probe. The Z position corresponds to the time delay from reception by the intravascular ultrasound imaging probe 352 to transmission by the external ultrasound imaging probe 356. A weighted average of positions of all elements of the intravascular ultrasound imaging probe 352 can be taken to identify an overall single position of the intravascular ultrasound imaging probe 352.

In the embodiment of FIG. 13, relative positions of each element are determined based on differences in intensity time delay, and/or phase. The true "up" position of the phased array corresponds to the element that indicates reception of the signal with the highest signal intensity and shortest time delay Δt, which in turn corresponds to the element(s) of the intravascular ultrasound imaging probe that face the external ultrasound imaging probe.

In the box formed by the broken dotted lines, amplitude of each received signal corresponds to the width and color of the cross (wider and darker indicates stronger amplitude). The Y axis of the chart shows the transmit delay Δt between the extravascular ultrasound imaging probe and the intravascular ultrasound imaging probe The received signals received by each element of the intravascular ultrasound imaging probe 352 are aligned in the X direction. Specifically, received signals for elements 28 to 52 of the intravascular ultrasound imaging probe are shown in the example of FIG. 13. The vertical segment in the Y direction above the X-direction bisector corresponds to the phase delay (Δt) for each signal as it travels from the external ultrasound imaging probe 356.

Figure 14:
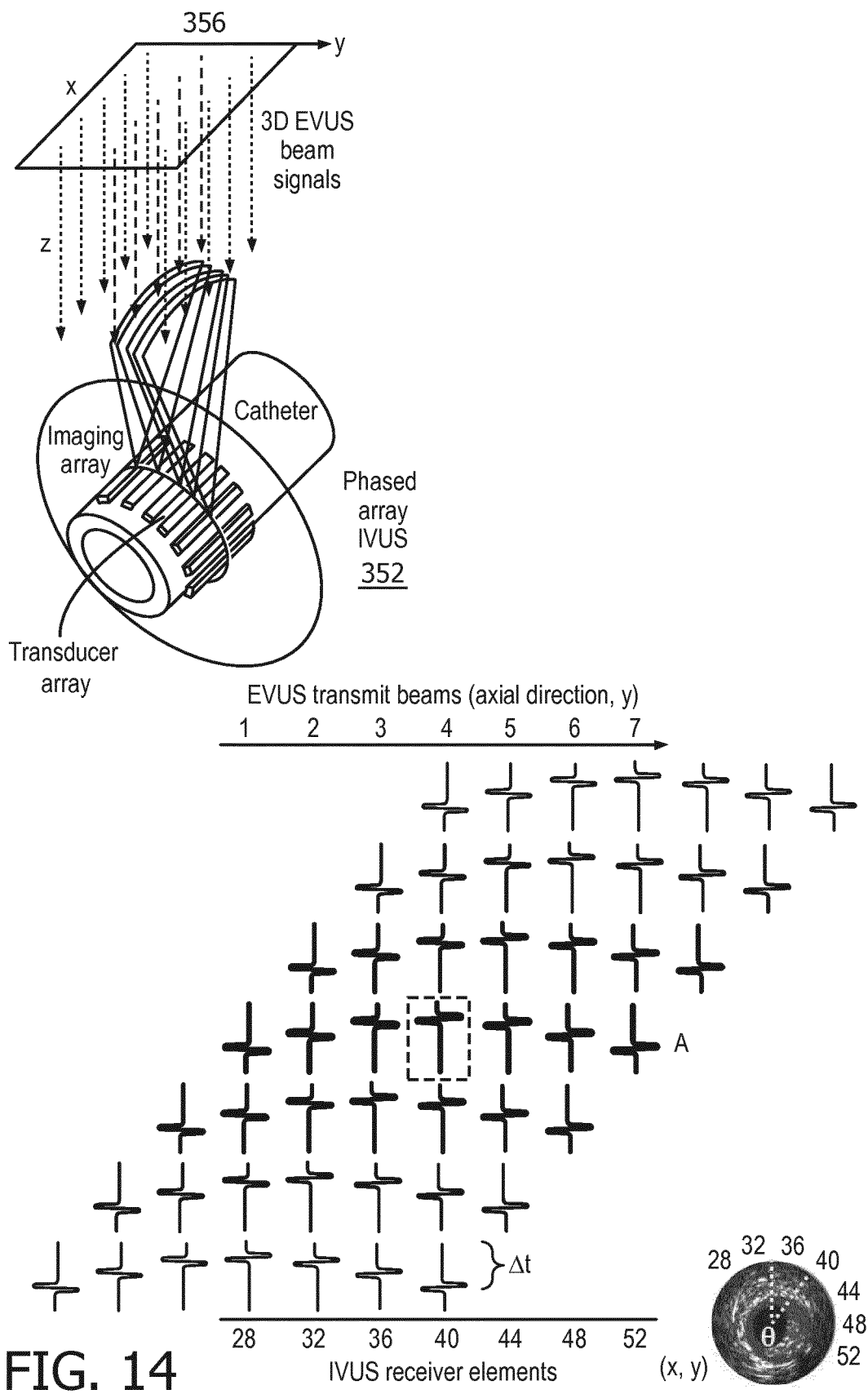
FIG. 14 illustrates a system with a phased array intravascular ultrasound and a 3-dimensional external ultrasound in intravascular ultrasound position identification, in accordance with a representative embodiment.

FIG. 14 illustrates a system with a phased array intravascular ultrasound and a 3-dimensional external ultrasound in intravascular ultrasound position identification, in accordance with a representative embodiment.

In the embodiment of FIG. 14, an intravascular ultrasound imaging probe 352 includes a phased array of elements. More particularly, multiple elements correspond to a predetermined configuration in/on the intravascular ultrasound imaging probe 352, and the external ultrasound imaging probe 356 is used to identify the relative locations of the multiple elements. The multiple elements are relatively fixed in place so as to repeatedly emit ultrasound beams and record reflected responses. Additionally, the multiple elements each include a passive ultrasound sensor that receives and reflects signals from the external ultrasound imaging probe 356. As an example, the multiple elements may be arranged in 36 positions each ten (10) degrees apart, so as repeatedly emit ultrasound beams and record reflected responses In the embodiment of FIG. 14, a 3-dimensional external ultrasound imaging probe 356 is used. Ambiguity due to out-of-plane direction is eliminated in the embodiment with the 3-dimensional external ultrasound imaging probe 356 whenever the intravascular ultrasound imaging probe 352 is within the volumetric field-of-view of the external ultrasound imaging probe 356. Here, the signals from the individual lines of the external ultrasound imaging probe 356 in the elevation direction are aggregated to determine which element of the intravascular ultrasound imaging probe 352 receives the maximum overall signal from the external ultrasound imaging probe 356. The maximum overall signal corresponds to the "up" direction and the minimum time delay Δt, which in turn corresponds to the element(s) of the intravascular ultrasound imaging probe that face the external ultrasound imaging probe.

The series of cross-shaped characters in FIG. 14 each reflect readings of signals from the external ultrasound imaging probe 356 received by an element of the intravascular ultrasound imaging probe 352. As noted in the drawing, the delay is indicated by Δt, which in turn reflects the leg of the cross in the Y direction above the horizontal cross section. Amplitude corresponds to the width and color of the cross markers (wider and darker indicates stronger amplitude). Each row of characters corresponds to an individual transmit beam from the external ultrasound imaging probe 356 and an individual element of the intravascular ultrasound imaging probe 352.

Figure 15:
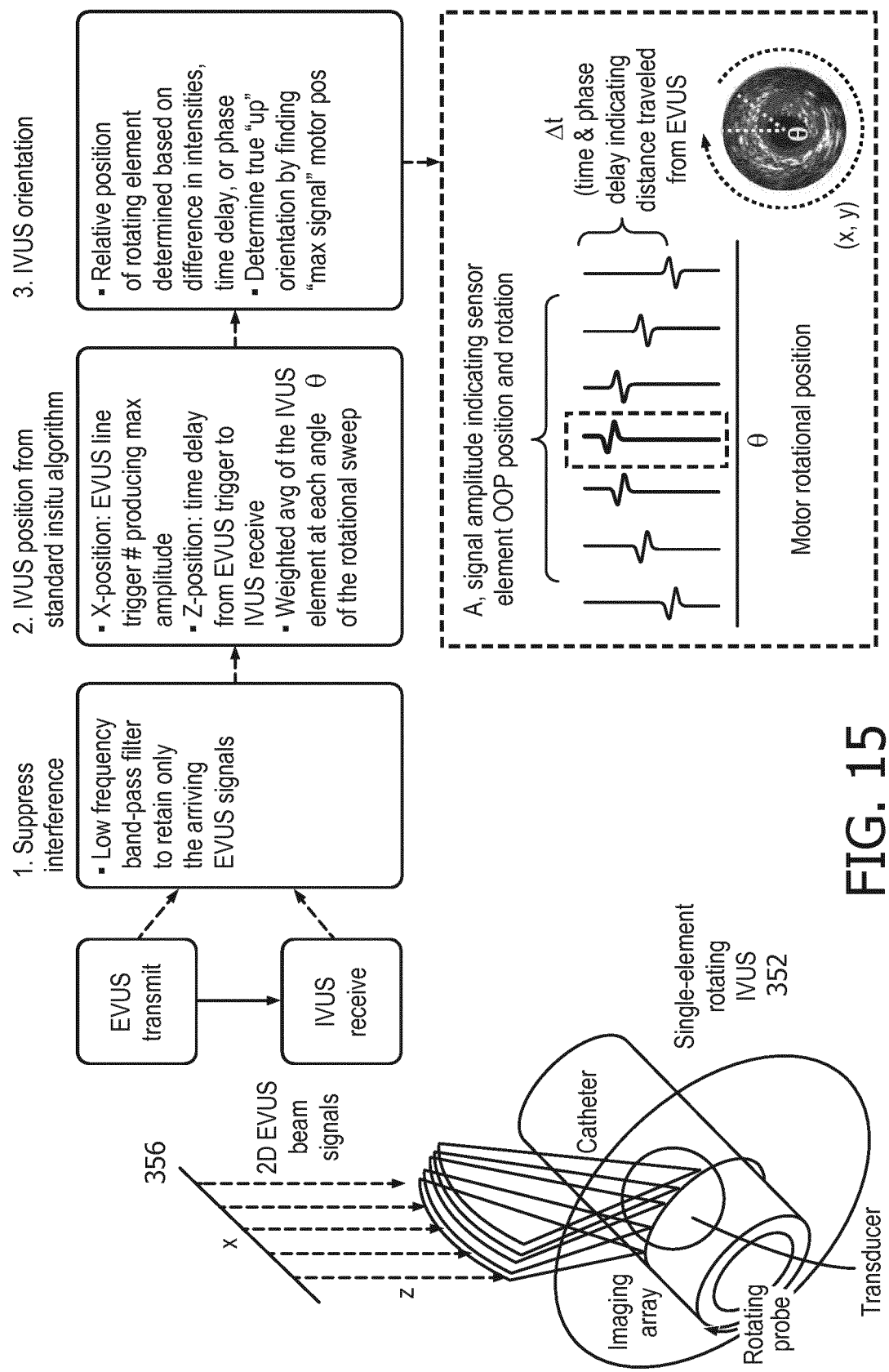
FIG. 15 illustrates a system with a single-element rotation intravascular ultrasound and a 2-dimensional or 3-dimensional external ultrasound in intravascular ultrasound position identification, in accordance with a representative embodiment.

FIG. 15 illustrates a system with a single-element rotation intravascular ultrasound and a 2-dimensional or 3-dimensional external ultrasound in intravascular ultrasound position identification, in accordance with a representative embodiment.

In the embodiment of FIG. 15, single-element rotation of an intravascular ultrasound element position is identified with either a 2-dimensional or 3-dimensional external ultrasound imaging probe 356. The single-element rotating intravascular ultrasound refers to an intravascular ultrasound imaging probe 352 in which a single element is rotated so as to repeatedly emit ultrasound beams and record reflected responses. As an example, a single element may be rotated to 36 positions each ten (10) degrees apart, so as repeatedly emit ultrasound beams and record reflected responses.

The "up" orientation corresponds to the motor position resulting in maximum signal amplitude and minimum time-of-flight delay through one 360° rotation. This differs markedly from a determination of an "up" position from an intravascular ultrasound imaging probe 352 with multiple elements in fixed positions relative to each other. For an external ultrasound imaging probe 356 that is 3-dimensional, the signals from the individual lines corresponding to the external ultrasound imaging probe 356 in the elevation direction are aggregated, as described for FIG. 14, to determine the "up" direction.

More particularly, in FIG. 15, a rotating probe rotates a single-element transducer so as to emit 2-dimensional ultrasound beams in three hundred sixty (360°) degrees. Multiple sets of 2-dimensional readings can then be combined to produce a 3-dimensional volume.

As shown, a low-frequency band-pass filter can be applied to retain only the arriving signals from the external ultrasound imaging probe 356. The position of the intravascular ultrasound imaging probe 352 in the X direction can be determined from a conventional algorithm in use for tracking interventional medical devices, by identifying which line trigger number (#) produces the maximum amplitude of a reflected signal from the intravascular ultrasound imaging probe 352 as it rotates. The position of the intravascular ultrasound imaging probe 352 in the Z direction can be determined from a time delay from the trigger of the external ultrasound imaging probe 356 to when the emitted ultrasound beam is received by the intravascular ultrasound imaging probe 352. The overall position of the intravascular ultrasound imaging probe 352 may be obtained from a weighted average of the first signal at each angle of the rotational sweep.

In FIG. 15, a relative position of the rotating element can be determined based on differences in intensities, time delay, and/or phase. The up position of the rotating element can be identified by finding the (received) signal with the maximum intensity, which should also correspond to the shortest time delay Δt, which in turn corresponds to the element(s) of the intravascular ultrasound imaging probe that face the external ultrasound imaging probe.

In the box formed by the broken lines in FIG. 15, the X axis of the chart shows the rotational position of the motor that rotates the single element of the intravascular ultrasound imaging probe 352. The width and color of the cross markers (wider and darker indicates stronger amplitude), and the Y axis of the chart shows the transmit delay Δt between the extravascular ultrasound imaging probe and the intravascular ultrasound imaging probe. As shown, the highest amplitude of the received signal corresponds to rotation of 0 degrees.

Figure 16:
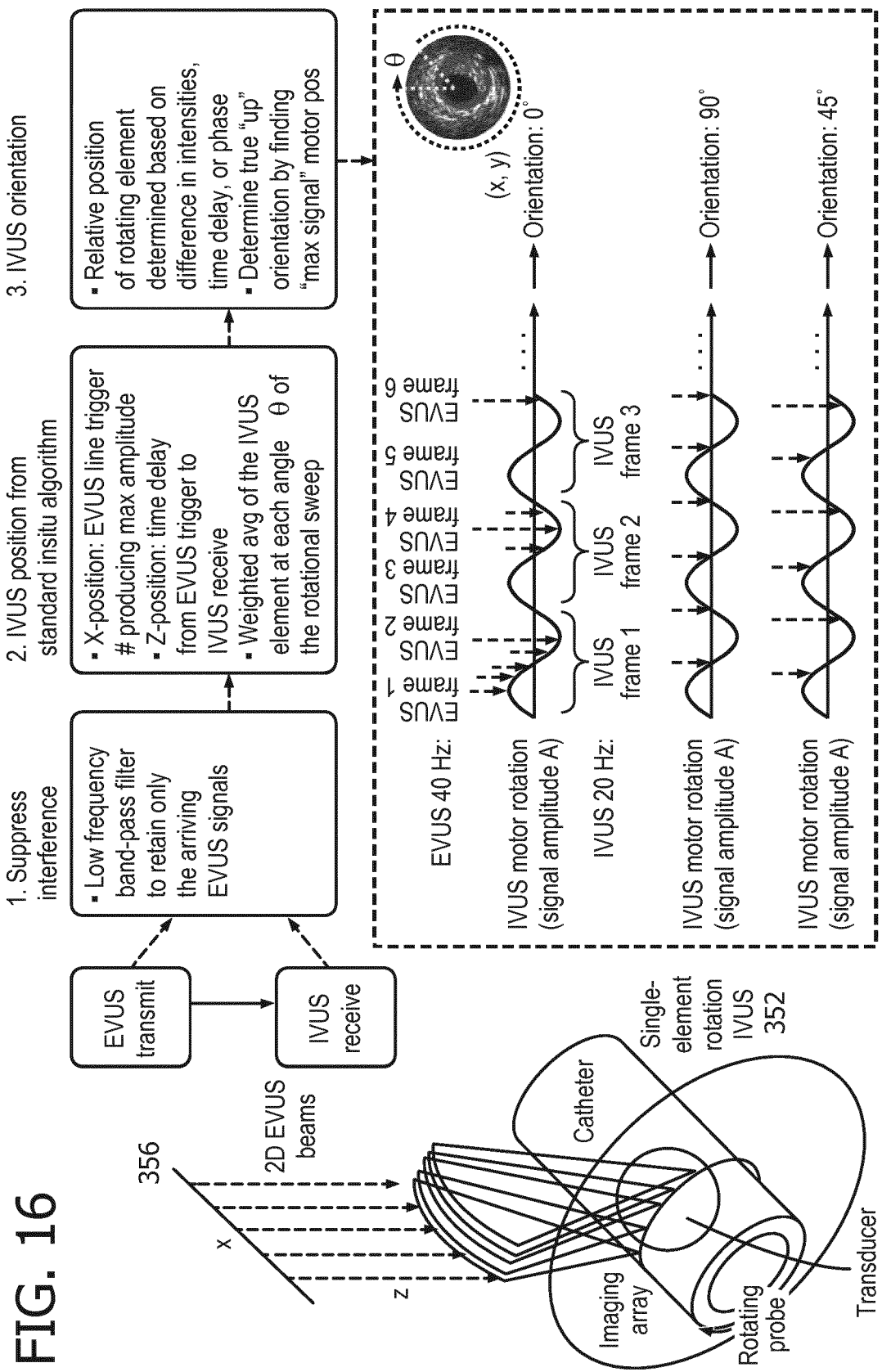
FIG. 16 illustrates a system with a single-element rotation intravascular ultrasound and a 2-dimensional or 3-dimensional external ultrasound in intravascular ultrasound position identification, in accordance with another representative embodiment.

FIG. 16 illustrates a system with a single-element rotation intravascular ultrasound and a 2-dimensional or 3-dimensional external ultrasound in intravascular ultrasound position identification, in accordance with another representative embodiment.

In the embodiment of FIG. 16, single-element rotation of an intravascular ultrasound element position is identified with either a 2-dimensional or 3-dimensional external ultrasound imaging probe 356. The single-element rotating intravascular ultrasound refers to an intravascular ultrasound imaging probe 352 in which a single element is rotated so as to repeatedly emit ultrasound beams and record reflected responses. As an example, a single element may be rotated to 36 positions each ten (10) degrees apart, so as repeatedly emit ultrasound beams and record reflected responses.

The intravascular ultrasound imaging probe 352 with a single element introduces an ambiguity in that signals received by the intravascular ultrasound imaging probe 352 are dependent on triggers from the external ultrasound imaging probe 356 along with the rotation of the single element in the intravascular ultrasound imaging probe 352. This ambiguity can be minimized if the frame rate of the external ultrasound imaging probe 356 is significantly higher than the frame rate of the intravascular ultrasound imaging probe 352. In other words, multiple frame may be captured by the external ultrasound imaging probe 356 with each 360° rotation of/by the motor of the intravascular ultrasound imaging probe 352. The "up" orientation then corresponds to the motor position resulting in maximum amplitude/minimum time-of-flight through one 360° IVUS rotation. For an external ultrasound imaging probe that is 3-dimensional, the signals from the individual lines corresponding to the external ultrasound imaging probe 356 in the elevation direction are aggregated, as described for FIG. 14.

More particularly, in FIG. 16, a rotating probe rotates a single-element transducer so as to emit 2-dimensional ultrasound beams in three hundred sixty (360°) degrees. Multiple sets of 2-dimensional readings can then be combined to produce a 3-dimensional volume.

As shown, a low-frequency band-pass filter can be applied to retain only the arriving signals from the external ultrasound imaging probe 356. The position of the intravascular ultrasound imaging probe 352 in the X direction can be determined from a conventional algorithm in use for tracking interventional medical devices, by identifying which line trigger number (#) produces the maximum amplitude of a reflected signal from the intravascular ultrasound imaging probe 352 as it rotates. The position of the intravascular ultrasound imaging probe 352 in the Z direction can be determined from a time delay from the trigger of the external ultrasound imaging probe 356 to when the emitted ultrasound beam is received by the intravascular ultrasound imaging probe 352. The overall position of the intravascular ultrasound imaging probe 352 may be obtained from a weighted average of the first signal at each angle of the rotational sweep. Moreover, a pose (or orientation) of the intravascular ultrasound imaging probe 352 can be identified by initially finding the up position of the rotating element using the strongest signal, and then determining relative positions of the rotation element based on differences in signal intensity, time delay, or phase.

In the box formed by the broken lines, frequency of the external ultrasound imaging probe 356 is noted as 40 hertz, and frequency of the intravascular ultrasound imaging probe 352 is 20 hertz. The lines show individual extravascular ultrasound imaging frames by the downward arrows, relative to the rotation orientations of the intravascular imaging probe indicated by the sinusoidal waves. For each set of signals, the highest orientation corresponds to zero (0) degrees, and the orientation proceeds to one hundred eighty (180) degrees and then back to zero (0) degrees.

Accordingly, intravascular ultrasound position identification enables better spatial context of intravascular ultrasound imagery, which may otherwise be difficult to interpret for non-expert uses due to the small field-of-view. By tracking the position and pose of the intravascular ultrasound imaging probe as it is advanced forward or pulled back through blood vessels, the exact position of individual two-dimensional circumferential images may be known. Such knowledge may then be used to stitch or otherwise fuse the individual two-dimensional images to form three-dimensional volumetric images with substantially greater field-of-view and contextual information.

Although intravascular ultrasound position identification has been described with reference to several exemplary embodiments, it is understood that the words that have been used are words of description and illustration, rather than words of limitation. Changes may be made within the purview of the appended claims, as presently stated and as amended, without departing from the scope and spirit of intravascular ultrasound position identification in its aspects. Although intravascular ultrasound position identification has been described with reference to particular means, materials and embodiments, intravascular ultrasound position identification is not intended to be limited to the particulars disclosed; rather intravascular ultrasound position identification extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A controller for identifying positioning of an intravascular ultrasound probe, the controller comprising: a memory configured to store instructions; and a processor configured to execute the instructions, and, when executed by the processor, the instructions cause the processor to: receive first signals from at least one imaging element of the intravascular ultrasound probe, wherein the first signals are imaging signals containing first image data generated by the intravascular ultrasound probe imaging an interior region of a vessel, receive second signals from an external ultrasound probe, wherein the second signals are imaging signals containing second image data generated by the external ultrasound probe imaging the vessel, wherein the first signals include first ultrasound signal components received by the at least one imaging element from the intravascular ultrasound probe and second ultrasound signal components received by the at least one imaging element from the external ultrasound probe, filter the second ultrasound signal component of each first signal received from the at least one imaging element, and determine, based on the first signals containing the first image data and the second signals containing the second image data, a position of the intravascular ultrasound probe in a tracking space that includes the intravascular ultrasound probe and the external ultrasound probe, wherein the position of the intravascular ultrasound probe is determined based on each of an amplitude, a phase, and a delay of the second ultrasound signal component of each first signal received from the at least one imaging element of the intravascular ultrasound probe.

2. The controller of claim 1, wherein, when executed by the processor, the instructions further cause the processor to:
determine based on the first signals and the second signals, a pose of the intravascular ultrasound probe in the tracking space,
wherein the first signals are received from a plurality of imaging elements of the intravascular ultrasound probe.

3. The controller of claim 2, wherein, when executed by the processor, the instructions further cause the processor to:
determine, based on the first signals from the plurality of imaging elements, relative positions of the plurality of imaging elements,
wherein the pose of the intravascular ultrasound probe is determined based on the relative positions of the plurality of imaging elements.

4. The controller of claim 1,
wherein the controller is provided as a hardware module that detachably interfaces with a system that includes the intravascular ultrasound probe.

5. The controller of claim 1, wherein, when executed by the processor, the instructions further cause the processor to at least one of:
compute the amplitude of each of the first signals from the at least one imaging element, compute the phase of each of the first signals from the at least one imaging element, and compute the delay of each of the first signals from the at least one imaging element.

6. The controller of claim 5, wherein, when executed by the processor, the instructions further cause the processor to:
determine, based on the at least one of the amplitude of each of the first signals, the phase of each of the first signals, and the delay of each of the first signals, relative positions of the at least one imaging element,
wherein a pose of the intravascular ultrasound probe is determined based on relative positions of each of the at least one imaging element.

7. The controller of claim 1, wherein, when executed by the processor, the instructions further cause the processor to:
control a display of the position of the intravascular ultrasound probe in the tracking space with a display of an ultrasound image produced by the intravascular ultrasound probe.

8. The controller of claim 7, wherein, when executed by the processor, the instructions further cause the processor to:
determine a sequence of positions of the intravascular ultrasound probe in the tracking space; and
control a display of the sequence of positions of the intravascular ultrasound probe in the tracking space with a display of ultrasound images produced by the intravascular ultrasound probe.

9. The controller of claim 1, wherein the first signals are used to determine one and only one position of the intravascular ultrasound probe; or wherein the first signals are used to determine a plurality of positions of the intravascular ultrasound probe based on differential characteristics of each of the at least one imaging element.

10. The controller of claim 1, wherein the controller is implemented as a component of a system that includes the intravascular ultrasound probe or as a component of a system that includes the external ultrasound probe.

11. The controller of claim 1, wherein the first signals and second signals are alternately processed based on alternative captures of frames by the intravascular ultrasound probe and the external ultrasound probe.

12. The controller of claim 1, wherein the first signals and second signals are simultaneously processed based on simultaneous captures of frames by the intravascular ultrasound probe and the external ultrasound probe.

13. The controller of claim 1, wherein the second image data generated by the external ultrasound probe includes the intravascular ultrasound probe and the position of the intravascular ultrasound probe is determined based further on location of the intravascular ultrasound probe in the second image data.

14. A method for identifying positioning of an intravascular ultrasound probe, the method comprising: receiving, by a controller, first signals from at least one imaging element of the intravascular ultrasound probe, wherein the first signals are imaging signals containing first image data generated by the intravascular ultrasound probe imaging an interior region of a vessel; receiving, by the controller, second signals from an external ultrasound probe, wherein the second signals are imaging signals containing second image data generated by the external ultrasound probe imaging the vessel; wherein the first signals include first ultrasound signal components received by the at least one imaging element from the intravascular ultrasound probe and second ultrasound signal components received by the at least one imaging element from the external ultrasound probe, filtering the second ultrasound signal component of each first signal received from the at least one imaging element, and determining, by the controller and based on the first signals containing the first image data and the second signals containing the second image data, a position of the intravascular ultrasound probe in a tracking space that includes the intravascular ultrasound probe and the external ultrasound probe, wherein the position of the intravascular ultrasound probe is determined based on each of an amplitude, a phase, and a delay of the second ultrasound signal component of each first signal received from the at least one imaging element of the intravascular ultrasound probe.

15. The method of claim 14, wherein the second image data generated by the external ultrasound probe includes the intravascular ultrasound probe and the position of the intravascular ultrasound probe is determined based further on location of the intravascular ultrasound probe in the second image data.

16. A system for identifying positioning of an intravascular ultrasound probe, the system comprising: the intravascular ultrasound probe configured to emit within a vessel first ultrasound waves configured to image an interior region of the vessel and generate first imaging signals containing first image data from imaging the vessel; an external ultrasound probe configured to emit external to the vessel second ultrasound waves configured to image the vessel and generate second imaging signals containing second image data from imaging the vessel; and a controller comprising a processor configured to: receive the first imaging signals containing the first image data from at least one imaging element of the intravascular ultrasound probe, wherein the first imaging signals include first ultrasound signal components received by the at least one imaging element from the intravascular ultrasound probe and second ultrasound signal components received by the at least one imaging element from the external ultrasound probe, receive the second imaging signals containing the second image data from the external ultrasound probe; and a filter circuit configured to filter the second ultrasound signal component of each first imaging signal received from the at least one imaging element, wherein the processor is further configured to determine, based on the first imaging signals containing the first image data and the second imaging signals containing the second image data, a position of the intravascular ultrasound probe in a tracking space that includes the intravascular ultrasound probe and the external ultrasound probe, wherein the position of the intravascular ultrasound probe is determined based on each of an amplitude, a phase, and a delay of the second ultrasound signal component of each first signal received from the at least one imaging element of the intravascular ultrasound probe.

17. The system of claim 16, wherein the second image data generated by the external ultrasound probe includes the intravascular ultrasound probe and the position of the intravascular ultrasound probe is determined based further on location of the intravascular ultrasound probe in the second image data.

* * * * *